US008883183B2

(12) United States Patent
Sullivan et al.

(10) Patent No.: US 8,883,183 B2
(45) Date of Patent: *Nov. 11, 2014

(54) MEDICAL DEVICES INCORPORATING COLLAGEN INHIBITORS

(75) Inventors: Christopher A. Sullivan, Winston-Salem, NC (US); Steve J. Hodges, Winston-Salem, NC (US); Anthony Atala, Winston-Salem, NC (US); James J. Yoo, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 556 days.

This patent is subject to a terminal disclaimer.

(21) Appl. No.: 12/130,614

(22) Filed: May 30, 2008

(65) Prior Publication Data

US 2009/0028914 A1 Jan. 29, 2009

(51) Int. Cl.
| *A61F 2/00* | (2006.01) |
| *A61L 27/54* | (2006.01) |
| *A61L 29/16* | (2006.01) |
| *A61L 31/16* | (2006.01) |

(52) U.S. Cl.
CPC .................. *A61L 27/54* (2013.01); *A61L 29/16* (2013.01); *A61L 31/16* (2013.01); *A61L 2300/432* (2013.01)
USPC ........................................................ 424/423

(58) Field of Classification Search
CPC . A61K 9/0024; A61K 9/0034; A61K 9/0043; A61K 9/0053; A61L 27/54; A61L 31/16; A61L 29/16
See application file for complete search history.

(56) References Cited

U.S. PATENT DOCUMENTS

| 4,291,687 | A | 9/1981 | Sinnreich |
| 4,485,088 | A | 11/1984 | Chvapil |
| 5,092,841 | A | 3/1992 | Spears |
| 5,263,927 | A | 11/1993 | Shlain |
| 5,385,935 | A | 1/1995 | Tamai et al. |

(Continued)

FOREIGN PATENT DOCUMENTS

| CA | 2603081 | 9/2013 |
| WO | WO 98/23244 | 6/1998 |

(Continued)

OTHER PUBLICATIONS

RD 476079, Dec. 2003.*

(Continued)

*Primary Examiner* — Bethany Barham
(74) *Attorney, Agent, or Firm* — Myers Bigel Sibley & Sajovec, P.A.

(57) ABSTRACT

Provided herein are implantable or insertable biomedical devices comprising a substrate and a collagen inhibitor on or in said substrate, and methods of treatment using the same. In some embodiments, the device is an absorbable esophageal or tracheal stent. In some embodiments, the device is a vascular stent. Wound closure devices are also provided herein, including a substrate and a collagen inhibitor on or in the substrate. Also provided are surgical packings, including a substrate and a collagen inhibitor on or in the substrate. A barrier material for preventing adhesions in a subject is further provided, including a preformed or in situ formable barrier substrate and a collagen inhibitor on or in the substrate. An ointment comprising a collagen inhibitor is further provided. Kits comprising the coated substrates are also provided.

37 Claims, 24 Drawing Sheets

(56) References Cited

U.S. PATENT DOCUMENTS

| | | | |
|---|---|---|---|
| 5,449,678 A * | 9/1995 | Pines et al. | 514/266.22 |
| 5,564,439 A | 10/1996 | Picha | |
| 5,685,860 A | 11/1997 | Chang et al. | |
| 5,723,448 A | 3/1998 | Gross et al. | |
| 5,755,788 A | 5/1998 | Strauss | |
| 5,852,024 A | 12/1998 | Pines et al. | |
| 6,028,078 A | 2/2000 | Hausheer et al. | |
| 6,046,340 A | 4/2000 | Seguin et al. | |
| 6,063,396 A | 5/2000 | Kelleher | |
| 6,090,814 A | 7/2000 | Nagler et al. | |
| 6,159,488 A | 12/2000 | Nagler et al. | |
| 6,224,630 B1 | 5/2001 | Bao et al. | |
| 6,239,177 B1 | 5/2001 | Mori et al. | |
| 6,281,262 B1 | 8/2001 | Shikinami | |
| 6,328,994 B1 * | 12/2001 | Shimizu et al. | 424/489 |
| 6,376,543 B1 | 4/2002 | Isaji et al. | |
| 6,420,371 B1 | 7/2002 | Pines et al. | |
| 6,638,917 B1 | 10/2003 | Li et al. | |
| 7,025,753 B2 | 4/2006 | Reever | |
| 7,097,857 B2 | 8/2006 | Tracy et al. | |
| 7,135,197 B2 | 11/2006 | Pena et al. | |
| 7,189,410 B1 | 3/2007 | Drohan et al. | |
| 2003/0108588 A1 | 6/2003 | Chen et al. | |
| 2003/0144727 A1 | 7/2003 | Rosenthal et al. | |
| 2004/0043052 A1 * | 3/2004 | Hunter et al. | 424/426 |
| 2005/0038498 A1 | 2/2005 | Dubrow et al. | |
| 2005/0187609 A1 | 8/2005 | Brar et al. | |
| 2005/0208095 A1 | 9/2005 | Hunter et al. | |
| 2005/0220882 A1 | 10/2005 | Pritchard et al. | |
| 2005/0234538 A1 | 10/2005 | Litvack et al. | |
| 2006/0020331 A1 | 1/2006 | Bates et al. | |
| 2006/0147492 A1 | 7/2006 | Hunter et al. | |
| 2006/0177480 A1 | 8/2006 | Sung et al. | |
| 2006/0204537 A1 | 9/2006 | Ratner et al. | |
| 2006/0229711 A1 | 10/2006 | Yan et al. | |
| 2006/0293351 A1 | 12/2006 | Pines et al. | |
| 2007/0038291 A1 | 2/2007 | Case et al. | |
| 2007/0048351 A1 | 3/2007 | Lunn | |
| 2007/0142339 A1 | 6/2007 | Whitehouse et al. | |
| 2007/0148205 A1 | 6/2007 | Whitehouse et al. | |
| 2007/0160640 A1 | 7/2007 | Jang et al. | |
| 2007/0299409 A1 | 12/2007 | Whitbourne et al. | |
| 2008/0095819 A1 | 4/2008 | Gourdie et al. | |
| 2008/0097580 A1 | 4/2008 | Dave | |
| 2008/0116106 A1 | 5/2008 | Lampropoulos et al. | |
| 2009/0171317 A1 | 7/2009 | Versi | |
| 2009/0226500 A1 | 9/2009 | Avelar et al. | |
| 2010/0021519 A1 * | 1/2010 | Shenoy | 424/423 |

FOREIGN PATENT DOCUMENTS

| | | | |
|---|---|---|---|
| WO | WO 02/36054 A1 | 5/2002 | |
| WO | WO 02/087586 A1 | 11/2002 | |
| WO | WO 2005/079703 A1 | 9/2005 | |
| WO | WO 2005-112999 A2 | 12/2005 | |
| WO | WO 2005-113031 A2 | 12/2005 | |
| WO | WO 2006/107957 A2 | 10/2006 | |
| WO | WO 2006/116989 A2 | 11/2006 | |
| WO | WO 2007-084396 A2 | 7/2007 | |

OTHER PUBLICATIONS

Bosher LH et al. The pathology of experimentally produced lye burns and strictures of the esophagus. The Journal of Thoracic Surgery. 1951: 483-489.

Burford TH et al. Caustic burns of the esophagus and their surgical management: a clinico-experimental correlation. Annals of Surgery. Sep. 1953; 139(3): 453-460.

McBride W et al. Restenosis after successful coronary angioplasty. The New England Journal of Medicine. Jun. 30, 1988; 318 (26): 1734-1737.

Lindner V et al. Role of basic fibroblast growth factor in vascular lesion formation. Circulation Research. 1991; 68(1): 106-113.

Baskin LS et al. Biochemical characterization and quantitation of the collagenous components of urethral stricture tissue. The Journal of Urology. Aug. 1993; 150(2 Pt 2): 642-7 Abstract only.

Granot I et al. Halofuginone: an inhibitor of type I synthesis. Biochimica et Biophysica Acta. Feb. 13, 1993; 1156(2): 107-112 Abstract only.

Choi ET et al. Halofuginone, a specific collagen type I inhibitor, reduces anastomotic intimal hyperplasia. Arch Surg. Jun. 1995; 130(6): 257-261.

Nyska M et al. Topically applied halofuginone, an inhibitor of collagen type I transcription, reduces peritendinous fibrous adhesions following surgery. Connective Tissue Research. 1996; 34(2): 97-103 Abstract only.

Nagler A et al. Inhibition of collagen synthesis, smooth muscle cell proliferation, and injury-induced intimal hyperplasia by halofuginone. Arteriosclerosis, Thrombosis, and Vascular Biology. Jan. 1997;17(1):194-202 Abstract only.

Liu K et al. Halofuginone inhibits neointimal formation of cultured rat aorta in a concentration-dependent fashion in vitro. Heart Vessels. 1998; 13(1): 18-23 Abstract only.

Nagler A et al. The effect of halofuginone, an inhibitor of collagen type I synthesis, on urethral stricture formation: in vivo and in vitro study in a rat model. The Journal of Urology; Nov. 2000; 164(5): 1776-1780.

Regar E et al. Stent development and local drug delivery. British Medical Bulletin. 2001; 59: 227-48.

Da Silva FA et al. Extracellular matrix changes in urethral stricture disease. The Journal of Urology. Aug. 2002; 168: 805-807.

Finn AV et al. A novel rat model of carotid artery stenting for the understanding of restenosis in metabolic diseases. Journal of Vascular Research. 2002; 39: 414-426 (Marked copy).

Shargal Y et al. Inhibition of anastomotic intimal hyperplasia by a synthetic nonsulphated heparin-mimicking compound. Exp Clin Cardiol. Autumn 2002; 7(2/3): 73-79.

Arbell D et al. Prevention of esophageal strictures in a caustic burn model using halofuginone, an inhibitor of collagen type I synthesis. Laryngoscope 2005; 115(9): 1632-5 Abstract only.

Ferguson DD. Evaluation and management of benign esophageal strictures. Diseases of the Esophagus. 2005; 18: 359-364.

Mitra AK and Agrawal DK. In stent restenosis: bane of the stent era. J Clin Pathol. 2006; 59: 232-239.

Tierney W et al. Enteral stents. Technology Evaluation Report. Gastrointestinal Endoscopy. 2006; 63(7): 920-926.

Kopecki Z et al. Collagen loss and impaired wound healing is associated with c-Myb deficiency. Journal of Pathology. 2007; 211: 351-361.

Maluenda G et al. A critical appraisal of the safety and efficacy of drug-eluting stents. Clinical Pharmacology & Therapeutics. May 2009; 85(5): 474-480.

Leigh Perkins LE. Preclinical models of restenosis and their application in the evaluation of drug-eluting stent systems. Veterinary Pathology. Jan. 2010; 47(1): 58-76.

Schembre D. Advances in esophageal stenting: the evolution of fully covered stents for malignant and benign disease. Adv Ther. 2010: 27(7): 413-425.

Sharma P et al. Role of esophageal stents in benign and malignant diseases. The American Journal of Gastroenterology. Feb. 2010; 105: 258-273.

Coronary stent. Wikipedia. Retrieved Nov. 13, 2010: 1 p.
Foley catheter. Wikipedia. Retrieved Nov. 13, 2010: 3 pp.
Uteric stent. Wikipedia. Retrieved Nov. 13, 2010: 3 pp.
Wound healing. Wikipedia. Retrieved Nov. 13, 2010: 15 pp.
Stenosis. Wikipedia. Retrieved Jan. 18, 2011: 2 pp.
Brodsky, "Anesthesia for Pulmonary Stent Insertion" Curr. Opin. Anaesthesiol. 16:65 (2003).

Brown et al., "Case 4. Pulmonary Stent Migration and Ingestion in a Lung Cancer Patient" J. Clin. Oncol. 24:1478 (2006).

Khan et al., "Double Stenting in Advanced Colorectal Cancer" BMJ Case Reports (Jan. 1, 2011).

"Bryan-Dumon™ Series II Rigid Bronchoscope" Bryan Corporation (2008) 12 pages.

"Carotid Wallstent®" Boston Scientific Corporation (2009) 11 pages.

(56) References Cited

OTHER PUBLICATIONS

"WallFlex® Biliary RX Stent" Boston Scientific Corporation (2009) 6 pages.
"WallFlex® Duodenal Stent" Boston Scientific Corporation (2007) 4 pages.
"WallFlex® Colonic Stent" Boston Scientific Corporation (2007) 4 pages.
"Polyflex® Esophageal Stent" Boston Scientific Corporation (2005) 4 pages.
"Dynamic™ (Y) Stent" Boston Scientific Corporation (2007) 2 pages.
"Evolution® Esophageal Controlled-Release Stent—Fully Covered" Cook Medical, Inc. (2011) 2 pages.
"Esophageal Z-Stents® with Z Speed Introduction System" Cook Medical, Inc. (2002) 2 pages.
"Zilver 518® RX Vascular Self-Expanding Stent" Cook Medical, Inc. (2009) 2 pages.
"Formula™ Renal Balloon-Expandable Stent" Cook Medical, Inc. (2011) 4 pages.
"Polaris™ Ultra Dual Durometer Ureteral Stent with Percuflex® Material and HydroPlus™ Coating" Boston Scientific Corporation (2004) 2 pages.
"Product Catalog" Cordis Corporation (2009) 124 pages.
"PROMUS® Everolimus Eluting Coronary Stent System" Boston Scientific Corporation (2011) 76 pages.
"TAXUS® Liberté®, TAXUS® Liberté® Atom™, TAXUS® Liberté® Long" Boston Scientific Corporation (2010) 21 pages.
"Plastic Stents Pancreatic and Biliary" Cook Medical, Inc. (2010) 29 pages.
Supplementary European Search Report and Examination Report, EP 07862365, Apr. 15, 2011.
"Palmoplantar pustulosis" from DermNetNZ, pp. 1-2 (http://dermnetnz.org/scaly/palmoplantar-pustolis.html), retrieved Sep. 23, 2011.
Nehls MC et al. Mithramycin Selectively inhibits collagen-$\alpha 1(l)$ gene expression in human fibroblast. J. Clin. Invest. (Dec. 1993) 92: 2916-2921.
*Retraction of:* [Nehls MC et al. Mithramycin Selectively inhibits collagen-$\alpha 1(I)$ gene expression in human fibroblast. J. Clin. Invest. (Dec. 1993) 92: 2916-2921] J. Clin. Invest. (Oct. 2003) 112(8): 1265.
Yamada H. et al. Tranilast, a selective inhibitor of collagen synthesis in human skin fibroblasts. J. Biochem. (Oct. 1994) 116(4): 892-897, Abstract only.
Chen S-J et al. Mithramycin inhibits myointimal proliferation after balloon injury of the rat carotid artery in vivo. Circulation (Nov. 1994) 90(5): 2468-73.
Nagler A. et al. Halofuginone—an inhibitor of collagen type I synthesis—prevents postoperative formation of abdominal adhesions. Annals of Surgery (1998) 227(4): 575-582.
Fishbein I et al. Local delivery of mithramycin restores vascular reactivity and inhibits neointimal formation in injured arteries and vascular grafts. Journal of Controlled Release (2001) 77: 167-181.
Sandorfi N et al. Inhibition of collagen gene expression in systemic sclerosis dermal fibroblasts by mithramycin. Ann Rheum Dis (2005) 64: 1685-1691.
Tanaka et al. Newly developed biodegradable stents for benign gastrointestinal tract stenosis: a preliminary clinical trial. Digestion (Mar. 6, 2006) 74: 199-205.
FDA Oncology Tools Product Label Details in Conventional Order for plicamycin, mithramycin. U.S. Food and Drug Administration. Supplemental No. 050109, 8 pp, May 30, 2008.
International Search Report and Written Opinion, PCT/US07/024615, mailed Apr. 3, 2008.

\* cited by examiner

MEDICAL DEVICES INCORPORATING COLLAGEN INHIBITORS

RELATED APPLICATIONS

This application is a continuation-in-part of application Ser. No. 11/948,294, filed Nov. 30, 2007, which claims the benefit of U.S. Provisional Patent Application Ser. No. 60/868,217, filed Dec. 1, 2006, the disclosure of each of which is incorporated by reference herein in its entirety.

This application is related to application Ser. No. 11/948,335, filed Nov. 30, 2007, and application Ser. No. 12/130,657, filed May 30, 2008, the disclosures of each of which is incorporated by reference herein in its entirety.

FIELD OF THE INVENTION

The present invention concerns medical devices, including implantable devices such as catheters and stents, as well as wound closure devices such as ointments, staples and sutures.

BACKGROUND OF THE INVENTION

Scar tissue forms in response to tissue injury after trauma. This response is mediated by multiple inflammatory pathways and involves the development of a complex matrix of collagen, hyaluronic acid, fibronectin, and proteoglycans (Salamone et al. *Current Otolaryngology*. McGraw Hill, 2006). Though relatively expedient, healing by scar tissue deposition (cicatrization) does not replace functional tissue by multi-germ layer regeneration.

Seventy million surgeries are performed annually in the United States, and with every surgery there is inevitable formation of scar tissue (DeFrances et al. *Advance Data From Vital and Health Statistics*. 2006 May; 371: 14). Fibrous adhesion formation after surgery or other trauma to tubular structures such as the esophagus, tracheobronchial tree, ureter, fallopian tubes and gut can lead to chronic illness and death. Scar tissue that forms in muscle, bone and skin tissue may lead to chronic orthopedic conditions, chronic pain, cosmetic deformity and decreased quality of life.

An example is paranasal sinus surgery. The paranasal sinuses are air spaces in the mammalian facial skeleton. These spaces can become obstructed due to various conditions such as allergy, infection, tumor, and radiation therapy. When conventional medical therapy fails, paranasal sinus surgery is a common procedure used to establish sinus drainage and to relieve the symptoms of sinus obstruction. Nearly 200,000 chronic sinus disease patients undergo sinus surgery that fails in more than 50% of cases due to unfavorable scar formation (Musy et al. *American Journal of Otolaryngology*. 2004 November-December; 25(6):418-22). Revision surgery has a higher complication rate than initial surgery, is less successful, and is associated with a perceived decrease in quality of life (Jiang et al. *Annals of Otology, Rhinology, and Laryngology*. 2002 February; 111(2):155-59).

Attempts to decrease scar tissue formation during wound healing such as with anti-inflammatory agents and inhibitors of fibroblast proliferation, are indirect and largely ineffective. These agents are non-specific, and not only inhibit fibroblasts, but also inhibit epithelial cell migration. In paranasal sinus surgery in particular, a cavity is created that must re-epithelialize with functional sinus lining (mucosa) that will promote active mucociliary clearance of sinus debris. In the treatment of tracheal stenosis, regeneration of respiratory epithelium is necessary for proper mucociliary transport and airway patency; therefore agents that inhibit re-epithelialization are counter productive to optimal healing in the paranasal sinus.

There is need for new approaches that will specifically target scar tissue without inhibiting germ layer regenerative tissue processes in order to alleviate scar tissue formation and other problems associated with medical interventions.

SUMMARY OF THE INVENTION

Provided herein are implantable or insertable biomedical devices comprising a substrate and a collagen inhibitor on or in said substrate. In some embodiments, the substrate includes a material selected from the group consisting of vinyl, polyethylene, poly(vinyl chloride) (PVC), ethylene vinyl acetate (EVA), silicone, latex, and polypropylene. In some embodiments, the collagen inhibitor is selected from the group consisting of: mithramycin, mitomycin-c, tranilast, halofuginone and analogs thereof.

Wound closure devices are also provided herein, including a substrate and a collagen inhibitor on or in the substrate. In some embodiments, the substrate is selected from the group consisting of biodegradable substrates and non-biodegradable (inert) substrates. In some embodiments, the device is a suture, staple, tape, or bandage. In some embodiments, the substrate includes a biodegradable polymer, e.g., poly(lactide)s, poly(glycolide)s, poly(lactide-coglycolide)s, poly (lactic acid)s, poly(glycolic acid)s, poly(lactic acid-co-glycolic acid)s, poly(caprolactone), polycarbonates, polyesteramides, polyanhydrides, poly(amino acid)s, poly (ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof, etc. In some embodiments, the substrate is a suture formed of braided, woven, or non-woven fiber material, e.g., silk, cotton, rayon, linen, wool, satin, nylon, polyester, polypropylene, polytetrafluoroethylene or combinations thereof. In some embodiments, the collagen inhibitor is selected from the group consisting of: mithramycin, mitomycin-c, tranilast, halofuginone and analogs thereof.

Also provided are surgical packings (e.g., sinus packings), including a substrate and a collagen inhibitor on or in the substrate. In some embodiments, the substrate includes a material selected from the group consisting of oxycellulose, methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, carboxymethylcellulose, microcrystalline cellulose, xanthan gum, silicon dioxide, and mixtures thereof. In some embodiments, the substrate is in the form of a dry powder. In some embodiments, the collagen inhibitor is selected from the group consisting of: mithramycin, mitomycin-c, tranilast, halofuginone and analogs thereof.

Methods of treating a paranasal sinus wound in a subject in need thereof are provided, including topically administering a collagen inhibitor in an amount effective to treat said wound. In some embodiments, the administering step is carried out by packing the paranasal sinus with a sinus packing material (e.g., a cellulose compound or gel) that includes a collagen inhibitor. In some embodiments, the collagen inhibitor is selected from the group consisting of: mithramycin, mitomycin-c, tranilast, halofuginone and analogs thereof.

Methods of treating esophageal or tracheal stricture in a subject in need thereof are also provided, comprising topically administering a collagen inhibitor in an amount effective to treat the stricture in the subject. In some embodiments, the administering step is carried out by stenting the stricture with a biodegradable stent comprising said collage inhibitor. In some embodiments, the collagen inhibitor is selected from the group consisting of: mithramycin, mitomycin-c, tranilast, halofuginone and analogs thereof.

A barrier material for preventing adhesions in a subject is further provided, including a preformed or in situ formable barrier substrate and a collagen inhibitor on or in the substrate. In some embodiments, the collagen inhibitor is selected from the group consisting of: mithramycin, mitomycin-c, tranilast, halofuginone and analogs thereof.

Methods of treating abdominal adhesions in a subject in need thereof are provided, including topically administering into the abdominal cavity of the subject a collagen inhibitor in an amount effective to treat said abdominal adhesions in said subject. In some embodiments, the collagen inhibitor is selected from the group consisting of: mithramycin, mitomycin-c, tranilast, halofuginone and analogs thereof.

An ointment or cream comprising a collagen inhibitor is also provided. In some embodiments, the collagen inhibitor is selected from the group consisting of: mithramycin, mitomycin-c, tranilast, halofuginone and analogs thereof. Methods of treating a wound (e.g., a skin wound) are provided, wherein the ointment or cream comprising a collagen inhibitor is topically administered to said wound.

Methods of treating coronary artery stenosis are provided, including topically administering a collagen inhibitor in an amount effective to treat said coronary artery stenosis. Methods of treating vascular stenosis of the cerebrovascular or peripheral vasculature are also provided, including topically administering a collagen inhibitor in an amount effective to treat said vascular stenosis. In some embodiments, the collagen inhibitor is selected from the group consisting of: mithramycin, mitomycin-c, tranilast, halofuginone and analogs thereof.

Kits including the implantable or insertable biomedical devices as described above are also provided.

The present invention is explained in greater detail in the specification set forth below.

DETAILED DESCRIPTION OF THE PREFERRED EMBODIMENTS

The disclosures of all United States Patent references cited herein are to be incorporated by reference herein as if fully set forth.

Figure 1:
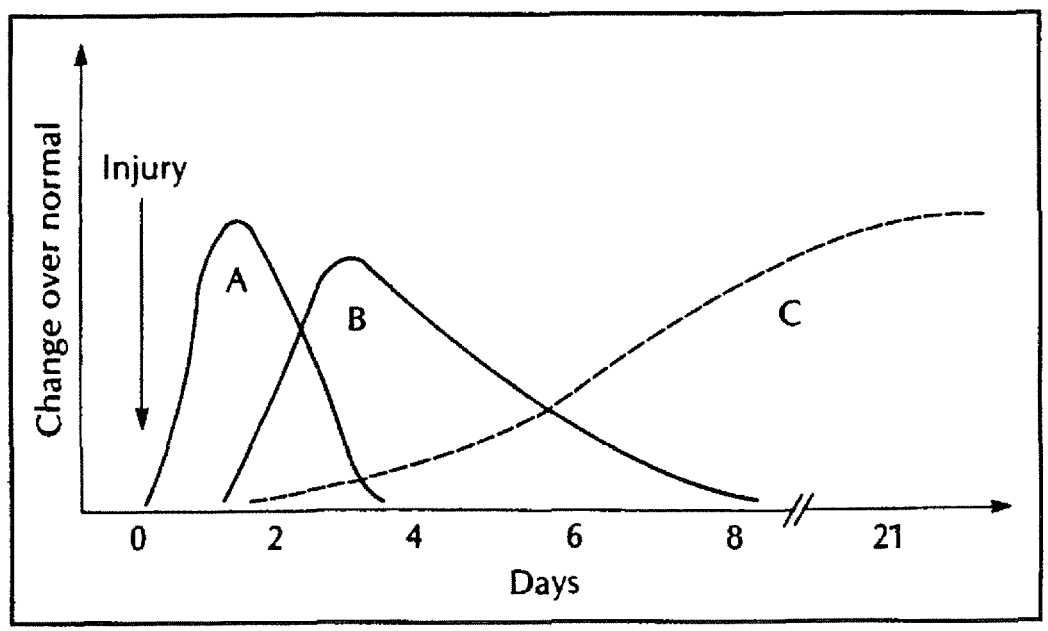
FIG. 1. Schematic diagram of the three phases of wound healing. A: Inflammation, B: Fibroplasia, C: Maturation FIG. 2. Scanning electron microscopy of HF—Br coated 3-0 Vicryl sutures (A) and uncoated 3-0 Vicryl sutures (B) at 200× magnification.

Healing through the deposition of scar (fibrous) tissue is the normal response to injury. In humans, the wound healing response is divided into three phases: inflammation, fibroplasias and maturation. The steps of the process overlap broadly and are best understood as a continuum rather than a series of discrete steps (FIG. 1).

Without wishing to be bound to any particular theory, the wound healing process begins with a disturbance of blood vessel integrity that exposes the subendothelial collagen to blood platelets. This event is the initiating step that leads to blood extravasation and triggers the acute inflammatory response. This response activates local and systemic factors that lead to an orderly and predictable migration of cells into the wound. The first cells to appear in the wound are neutrophils, followed by monocytes and fibroblasts. Fibroblasts are the dominant cell type during fibroplasia. This phase is characterized by fibroblast proliferation and migration. The major function of the fibroblast during this stage is to elaborate interstitial matrix and collagen type-1. It is this collagen that makes up the fibrous tissue that characterizes the clinical entity referred to as scar tissue. When the fibroplasia stage is complete, the final stage of maturation occurs during which the wound becomes acellular and undergoes remodeling over months to years. During the remodeling phase the wound gathers tensile strength. Under the influence of various mediators and enzymes, remodeling is thought to represent the interplay between matrix synthesis and degradation.

Provided herein are compositions, devices and methods of treatment to improve wound healing after medical procedures such as surgery or other trauma. In some embodiments, the present invention provides collagen inhibitors topically administered to the wound or site of injury.

"Stenosis" or "stricture" refers to the narrowing of a bodily canal, passageway or tubular structure or organ. Similarly, "restenosis" is the recurrence of a narrowing of a bodily canal, such as a blood vessel.

A "capsule" is a cover or envelope partially or wholly surrounding a structure in the body. Capsules containing collagen fibers form as a normal reaction around a foreign substrate implanted in the body (e.g., breast implants, pacemakers, orthopedic joint prosthetics), tending to wall it off. However, certain implants may function better with less capsule formation. See, e.g., U.S. Pat. No. 5,564,439 to Picha.

"Subjects" that may be treated by the present invention include both human subjects for medical purposes and animal subjects for veterinary and laboratory purposes. Other suitable animal subjects are, in general, mammalian subjects such as primates, bovines, ovines, caprines, porcines, equines, felines, canines, lagomorphs, rodents (e.g., rats and mice), etc. Human subjects are the most preferred. Human subjects include fetal, neonatal, infant, juvenile, adult and geriatric subjects.

"Treat" as used herein refers to any type of treatment or prevention that imparts a benefit to a subject afflicted with or at risk of developing scarring or complications involving scar tissue production and/or collagen production, including improvement in the condition of the subject (e.g., in one or more symptoms), delay in the progression of the scarring, delay the onset or slow the progression of collagen deposition, capsule formation, stricture, restenosis, scarring, etc. As such, the term "treatment" also includes prophylactic treatment of the subject to prevent the onset of symptoms. As used herein, "treatment" and "prevention" are not necessarily meant to imply cure or complete abolition of symptoms, but refer to any type of treatment that imparts a benefit to a patient afflicted with a disease, including improvement in the condition of the patient (e.g., in one or more symptoms), delay in the progression of the disease, etc.

"Treatment effective amount", "amount effective to treat" or the like as used herein means an amount of the collagen inhibitor sufficient to produce a desirable effect upon a patient inflicted with wounds or site of injury. This includes improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

I. Collagen Inhibitors

"Collagen inhibitors" useful for carrying out the present invention are known and include all agents that inhibit the synthesis of collagen. See, e.g., U.S. Pat. Nos. 6,046,340 and 5,092,841; PCT Publication No. WO/2005/112999. Collagen is the major protein component of the extracellular matrix in organisms. There are at least 12 types of collagens, with types I, II and III being the most common. They are primarily synthesized in the body by fibroblasts during healing, and are formed by processing of the precursor procollagen proteins.

In some embodiments, inhibitors of type-1 collagen (also known as type I collagen) are preferred. The primary component of scar tissue, collagen type-1alpha, typically forms a protein rod 300 nm long composed of 3 subunits: two $\alpha 1(I)$ chains and one $\alpha 2(I)$ chain. Within the fibroblast, elaboration of type-1 collagen is controlled by activation of the alpha-1 collagen gene. Therefore, in some embodiments, inhibitors of the alpha-1 collagen gene expression are preferred.

Examples of "collagen inhibitors" as used herein include, but are not limited to, mithramycin, mitomycin-c, tranilast, halofuginone, d-penicillamine, beta-aminopropionitrile, okadaic acid, LY294002 (PI-3K inhibitor), 5-fluorouracil, analogs thereof, etc.

Mithramycin (MIT or plicamycin) is an aureolic acid polyketide antibiotic that binds to GC-rich areas of DNA. See, e.g., U.S. Pat. No. 5,723,448. It is a parental cell cycle-phase nonspecific antineoplastic agent derived from *Streptomyces plicatus*, a gram-positive soil bacterium. Mithramycin was originally developed as an antibiotic with activity primarily against gram-positive bacteria (Grundy et al., "Aureolic acid, a new antibiotic." *Antibiotics and Chemotherapy*. III (12) December (1953):1215-1220). Since then, it has been used as a chemotherapeutic agent to treat testicular cancer and to manage malignant and other causes of hypercalcemia. Mithramycin acts as an intercalating agent, inserting between base pairs and causing the double helix to uncoil, thus preventing DNA synthesis and transcription from taking place ("Plicamycin" Online drug information (WFUSM). Gold Standard Inc. 2007). It is currently administered to patients via intravenous infusion only. More recently, mithramycin has been suggested as a treatment for Huntington's disease (Ferrante, et al. "Chemotherapy for the Brain: The Antitumor Antibiotic Mithramycin Prolongs Survival in a Mouse Model of Huntington's Disease." *J. Neurosci.* 2004; 24(46): 10335-10342).

A 1993 study by Nehls et al. reported that mithramycin inhibits collagen-α1(I) gene expression in human fibroblast cells (J. Clin. Invest. 92:2916-2921). However, this publication was retracted 10 years later, in 2003 (J. Clin. Invest. 112:1265). A 2005 study by Sandorfi et al. reported that mithramycin could inhibit collagen production and gene expression in systemic sclerosis dermal fibroblasts cultured in vitro (*Ann. Rheum Dis.* 64:1685-1691).

Systemic (high) dosing of mithramycin in humans (e.g., 25-30 mg/kg) can interfere with systemic collagen homeostasis and is associated with grave side effects (bleeding, tissue necrosis and death) and has necessitated a black box warning by the U.S. Food and Drug Administration (U.S. Food and Drug Administration• Center for Drug Evaluation and Research FDA Oncology Tools Product Label Details in Conventional Order for plicamycin, mithramycin. Supplement number: 050109). To avoid systemic side effects, in some embodiments of the present invention, mithramycin is administered topically at the site of injury/stenting, in low (e.g., microgram) doses to achieve minimum concentrations in vitro and in vivo in the range of $10^{-9}$ to $10^{-5}$ M.

Mitomycin-c is a known fibroblast inhibitor with known scar inhibitory effects in the eye, sinus, larynx, trachea and pharyngoesophagus.

Tranilast (2-(2,3-dimethoxycinnamoyl)aminobenzoic acid) is also known and described in, for example, U.S. Pat. Nos. 5,385,935; 6,239,177; and 6,376,543.

"Halofuginone" or halofuginone bromide (7-bromo-6-chloro-3-[3-(3-hydroxy-2-piperidinyl)-2-oxopropyl]-4(3H) is known and described in, for example, U.S. Pat. Nos. 5,449,678, 6,420,371; 6,028,078; 6,090,814; and 6,159,488. Halofuginone is a quinazolinone compound that has been used in the cattle and poultry industries as an anti-coccidal agent. Serendipitously, it was discovered that dermal thinning was occurring in chickens that were administered the drug systemically. Further study of this phenomenon led to the discovery that the mechanism of action of halofuginone was inhibition of the alpha-1 collagen gene promoter (Granot I et al. *Poult Sci.* 1991 July; 70(7):1559-63). The pharmacology of this compound has been extensively studied for veterinary use and has FDA orphan drug approval for use in humans to treat seleroderma.

II. Substrates

Substrates include any biocompatible substrate, and may be biodegradable or non-biodegradable.

Biodegradable or bioabsorbable substrates may be formed of biodegradable polymers. Any suitable polymer may be employed, including, but not limited to, poly(lactide)s, poly (glycolide)s, poly(lactide-coglycolide)s, poly(lactic acid)s, poly(glycolic acid)s, poly(lactic acid-co-glycolic acid)s, poly (caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, as well as blends and copolymers thereof. See, e.g., U.S. Pat. No. 7,097,857.

According to some embodiments, the present invention provides a wound closure device comprising a substrate and a collagen inhibitor on or in said substrate. The substrate may comprise, consist of or consist essentially of a biodegradable substrate (such as albumin, collagen, synthetic polyamino acids, prolamines, polysaccharides, etc., or biodegradable polymers such as polylactides, polyglycolic acids, poly(lactide-co-glycolides), polycaprolactones, polycarbonates, polyamides, polyanhydrides, polyamino acids, polyortho esters, polyacetals, polycyanoacrylates, and degradable polyurethanes) or a non-biodegradable (inert) substrates such as silicone and silk, or polyvinyl alcohol, polyethylene, polyurethane, polypropylene, polycaprolactone, polyacrylates, ethylene-vinyl acetates, polystyrenes, polyvinyl oxides, polyvinyl fluorides, poly(vinyl imidazoles), chlorosulphonated polyolefins, polyethylene oxides, polytetrafluoroethylenes, nylons, and copolymers and combinations thereof. The device may take any suitable form, such as a suture, staple, tape, or bandage. In some embodiments the collagen inhibitor is carried in a biodegradable polymer which is coated on an inert or non-biodegradable substrate.

In some embodiments the device is a suture. Sutures may be formed of biodegradable polymers as described above (which may be in the form of a unitary solid), or may be formed from braided, woven, or non-woven fiber material (e.g., silk, cotton, rayon, linen, wool, satin, nylon, polyester or mixtures thereof). See, e.g., U.S. Pat. Nos. 5,685,860 and 6,224,630. In some embodiments, sutures include polypropylene (e.g., prolene or marlex) and/or polytetrafluoroethylene (PTFE) (e.g., Gore-Tex).

The present invention also provides surgical packings (e.g., sinus packings) that include a substrate and a collagen inhibitor on or in said substrate. The packing may take any suitable form, including, but not limited to, those described in U.S. Pat. Nos. 5,263,927 and 4,291,687.

The substrate material for the packing may be formed of any suitable material, including but not limited to methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, carboxymethylcellulose, microcrystalline cellulose, xanthan gum, silicon dioxide, and mixtures thereof. See, e.g., U.S. Pat. No. 7,135,197. Oxycellulose is currently used as a wound packing to achieve hemostatis. In some embodiments the substrate may be provided in the form of a dry, preferably sterile, powder (e.g., with which the collagen inhibitor may be mixed).

In some embodiments, a barrier material is used for preventing adhesions in a subject, comprising in combination, a preformed or in situ formable barrier substrate and a collagen inhibitor on or in said substrate. The substrate may be any suitable material, and when formed in situ any suitable cross-linking agent may be employed. Suitable examples include but are not limited to those described in U.S. Pat. No. 6,638, 917. The substrate or material may be bioabsorbable (e.g., a hemostatic material) or non-bioabsorbable (e.g., a non-absorbable mesh, such as is currently used in hernia repair).

A further aspect of the invention is an implantable or insertable biomedical device comprising a substrate and a collagen inhibitor on or in said substrate. In some embodiments, the device is a urethral, ureteral, or nephroureteral catheter or stent. Various nasal, esophageal and tracheal stents are also known. Cranial, maxillary and mandibular bone plates include bioabsorbable substrates (such as poly-L-lactic-polyglycolic plates (PLLA/PGA)) and non-bioabsorbable substrates (such as titanium or other metals).

In some embodiments, a non-bioabsorbable stent (i.e., a tube designed to prevent luminal strictures) anywhere in the body. Examples include, but are not limited to, Urethral catheter, Ureteral stent, Nephroureteral catheter, Esophageal stent, Tracheostomy stent, Gastric feeding tube, Nasogastric tube, Laryngeal/tracheal/pulmonary stent, Myringotomy tube, Nasal stent, Salivary duct stent, Biliary stent, Enteric stents, Nasolacrimal stents.

Still other examples are described below. The substrate may be comprised of any suitable biodegradable or non-biodegradable material. In some embodiments the substrate (e.g., from which the catheter is formed) comprises a material such as vinyl, polyethylene, poly(vinyl chloride) (PVC), ethylene vinyl acetate (EVA), silicone, latex, or polypropylene. See, e.g., U.S. Pat. No. 7,025,753. The collagen inhibitor may be coated on such a substrate material, with or without a carrier (such as a biodegradable polymer), by any suitable technique as discussed further below.

Specific examples of devices or products that can be used to carry out the present invention by including a collagen inhibitor on or in a substrate from which the product or device is formed include, but are not limited to (for various fields):

Urology:
Coated Urethral Catheter
Coated Ureteral Stent
Coated Nephroureteral Catheter
ENT:
Coated Sinus Packing Material
Injectable sinus packing material
Coated Esophageal Stent
Coated Tracheostomy Tube
Coated Gastric Feeding Tube
Coated Nasogastric Tube
Coated Laryngeal/Tracheal/Pulmonary Stent
Injectable Material for Vocal Fold Augmentation
Coated Myringotomy Tube
Coated Nasal Septal Splint
Coated Nasal Stent
Coated Salivary Duct Stent
Coated Laryngeal Implant
Injectable gel for salivary radiation fibrosis
Coated cranial, maxillary, mandibular absorbable and nonabsorbable bone plates
Plastic Surgery/Dermatology:
Coated Silicone Implants (or Coated Implants of other Composition)
Injectable Material for Cosmetic Augmentation (Bulking Agent)
Cream/Gel/Spray for Prevention of Hypertrophic Scar
Coated Silicone Sheets for the Prevention of Scarring
Cream/Gel/Spray/Silicone Sheets to Prevent Burn Scarring/Contractures
Coated skin graft material
Coated Suture for Wound Closure
Coated Skin Staples/Intracorporeal Staples
Coated "Steri-Strips" Wound Closure Adhesives
General Surgery:
Coated Sheets or Sprays for the Prevention of Surgical Adhesions
Coated Biliary Stents
Coated Enteric Stents
Ophthalmology
Coated Nasolacrimal Stents
Vascular Surgery:
Coated Endovascular Stents
Cardiology:
Coated Endovascular Cardiac Stents
Orthopaedic:
Coated absorbable and nonabsorbable bone plates
Miscellaneous:
Coating for other Implanted Artificial Medical Devices (vascular access devices, insulin pumps, etc)
Coated synthetic polymers [e.g., polyglycolic acid (PGA), polylactic acid (PLA), and poly(lactic-co-glycolic acid) (PLGA)], used to make absorbable vascular stent, cardiovascular stents, staples, suture Devices, materials, and compositions of the invention may be used in the treatment of both human subjects and animal subjects such as dogs, cats, horses, cattle, sheep, monkeys, etc. for veterinary or laboratory purposes.

III. Formulations

In some embodiments, collagen inhibitors of the present invention are provided as a coating on a substrate. Collagen inhibitors may be coated on a substrate by any suitable technique, such as dipping, spraying, spray drying, etc. The collagen inhibitor may be applied per se or concurrently with a carrier material or film-forming material, such as a biodegradable polymer (e.g., as described above). Collagen inhibitors may be combined into materials (such as powders or biodegradable materials) by any suitable technique, such as mixing, co-extruding, etc. In some embodiments, the collagen inhibitor is included in an amount effective to inhibit scar formation and/or collagen formation on or adjacent the implanted or inserted substrate.

According to some embodiments, for suture and/or packing materials the coating process includes one or more of the following steps: (a) prepare materials to desired size and shape for implantation; (b) prepare a solution of a collagen inhibitor (e.g., HFBr at 0.5 µg/ml); (c) modify surface of material by flash freeze in liquid nitrogen, microwave heat (15-30 seconds) or plasma reactor to enhance adherence properties; (d) materials are then dipped and immediately frozen at −80 F for approximately 24 hours; (e) Frozen materials are then lyophilized (i.e., vacuum dried); 69 materials are sterilized, e.g., using ethylene oxide or gamma irradiation.

According to some embodiments, coating and/or impregnating stent materials (e.g., for esophagus, trachea, vascular, etc.) with a collagen inhibitor includes one or more of the following steps: (a) dry collagen inhibitor (e.g., HFBr, mithramycin, etc.) in powder form is mixed (e.g., in a 50:50 ratio) with stent material also in powder form (e.g., PLLA, PGA, Vicryl (polygalactin)); (b) powder material is solubilized in a suitable solution and electrospun into desired shape (in some embodiments, this process results in a collagen inhibitor impregnated stent that allows freedom to make the desired shape for implantation); (c) stent is sterilized, e.g., using ethylene oxide or gamma irradiation.

According to some embodiments, wound glue including a collagen inhibitor includes one or more of the following steps: (a) the collagen inhibitor (e.g., HFBr at 0.5 µg/ml) is mixed 50:50 with a suitable glue material (e.g., acrylate material); and (b) applied directly to the wound. In other embodiments, collagen inhibitor is mixed with carboxymethylcellulose and applied directly to the wound.

In some embodiments, formulations containing a collagen inhibitor as described herein may be applied as a topical ointment or cream containing the collagen inhibitor(s). When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (e.g., PEG400, PEG3350, etc.), and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

According to some embodiments, coating of stents (e.g., permanent catheters) with a collagen inhibitor includes one or more of the following steps. (a) Weigh stent; (b) Modify surface of the stent with a plasma reactor, or alternatively microwave water wet stent for about 30-60 seconds; (c) Immerse stent in collagen inhibitor (e.g., halofuginone) and freeze in liquid nitrogen or −80 C); (d) Lyophilize stent (e.g., overnight); (e) Weigh stent; 69 Immerse stent in 1% PEG (3500-5000 g/mol filtered in 0.2 um filter); (g) Freeze PEG in liquid nitrogen or −80 C, and lyophilize overnight; (h) Immerse stent in collagen inhibitor (e.g., halofuginone) and freeze and lyophilize overnight; (i) Weigh stent; and (j) Sterilize.

According to some embodiments, coating of stents (e.g., permanent catheters) with a collagen inhibitor includes one or more of the following steps. (a) Weigh stent (b) Modify surface of the stent with a plasma reactor, or alternatively microwave wet stent (e.g., wet with PBS and covered with PBS soaked gauze) for about 30-60 seconds; (c) Dip stent in 2% PLGA-COOH to cool; (d) Dry under hood; (e) Cover with soaked gauze (e.g., with PBS) and microwave for about 30-60 seconds (or use plasma reactor); 60 Coat stent with halofuginone (e.g., immerse) and freeze in liquid nitrogen and lyophilize overnight; (g) Weight stent to estimate drug content; and (h) Sterilize.

Those of skill in the art will appreciate that all of the above methods can be modified and optimized as desired by routine methods without departing from the spirit of the invention disclosed herein.

IV. Dosages and Routes of Administration

In preferred embodiments, collagen inhibitors of the present invention are administered topically (i.e., locally) to the wound or site of injury. In some embodiments, compositions including collagen inhibitors may be administered via a coated suture, via combination with a gel or suitable wound glue, via coatings and/or impregnating collagen inhibitors onto a suitable substrate as described herein.

In some embodiments, topical application of one or more collagen inhibitors in nano ($10^{-9}$) or pico ($10^{-12}$) molar doses is sufficient to inhibit collagen type-1 production in an open wound. In some embodiments, collagen inhibitors is used topically as a packing material (e.g., in the sinus after paranasal sinus surgery) to prevent post-operative scar tissue formation.

In some embodiments, collagen inhibitors are administered by elution/absorption of the drug in less than 30 minutes. In some embodiments, administration is performed over a longer period of time, e.g., substantial elution over 30 minutes, 1, 2 or 3 hours, and up to 5, 6, 7 or 8 days. In some embodiments, collagen inhibitors are eluted over time to capture as much of the early fibroplasia stage of wound healing as possible (e.g., over 3-7 days). In some embodiments, elution occurs at a differential rate, with early elution independent of substrate degradation and later elution that is dependent upon substrate degradation.

For example, in some embodiments, the collagen inhibitor is administered in a single or total dosage over time of less than 1 mg. In some embodiments, the collagen inhibitor is administered in a range of $10^{-6}$, $10^{-7}$, $10^{-8}$ or $10^{-10}$, $10^{11}$ or $10^{-12}$ molar doses.

In some embodiments, formulations containing a collagen inhibitor (e.g., HF, mithramycin, etc.) may be applied as a topical ointment or cream containing the active ingredient(s) in an amount of, for example, 0.005 to 5% w/w (including active ingredient(s) in a range between 0.01% and 1% in increments of 0.05% w/w such as 0.05% w/w, 0.1% w/w, 0.5%, etc.), preferably 0.01 to 1% w/w, and most preferably 0.05 to 0.5% w/w. In some embodiments, formulations contain a collagen inhibitor in sufficient amount/concentration to deliver a target tissue dose in the microgram range with molar concentrations of $10^{-5}$ M to $10^{-9}$ M.

In some embodiments, collagen inhibitors are administered at a dosage level such that collagen inhibition is achieved with little to no cell toxicity. In some embodiments, collagen inhibitors are administered at a dosage sufficient to achieve a tissue level for the days of drug elution between $10^{-7}$ to $10^{-12}$ molar doses.

In other embodiments (e.g., paranasal sinus), collagen inhibitors (e.g., HF, mithramycin, etc.) is delivered topically as a single dose of between 50 and 500 micrograms (e.g., 100-300 micrograms) to achieve tissue effect (e.g., while achieving in vitro molar concentrations between $10^{-5}$ M and $10^{-9}$ M in 3 cc PBS). In yet other embodiments (e.g., trachea) up to 500 micrograms of collagen inhibitor is given topically to achieve tissue effect (e.g., while achieving in vitro molar concentrations between $10^{-5}$ M and $10^{-9}$ M in 3 cc PBS). In other embodiments (e.g., skin) 10 micrograms is sufficient to achieve tissue effect without affecting tensile strength of dermal wounds (e.g., while achieving in vitro molar concentrations between $10^{-5}$ M and $10^{-9}$ M in 3 cc PBS).

Some embodiments of present invention are explained in greater detail in the following non-limiting examples.

EXAMPLES

Example 1

Effect of a Collagen Type-I Inhibitors Halofuginone, on Dermal Wound Healing

Halofuginone has been used in experimental animal models as a systemic agent to inhibit scar formation (Pines et al. *General Pharmacology*. 1998 April; 30(4):445-50; Pines et al. *Biol Blood Marrow Transplant*. 2003 June; 9(7):417-25). However, little is know about its effectiveness as a topical agent for this purpose.

Experimental models for wound healing and scar tissue formation are well described in the rat, and all incorporate dorsal skin incisions (Kapoor et al. *The American Journal of Pathology*. 2004; 165:299-307). The rat has a relatively thick dermis on the dorsum that approximates the thickness of human dermis.

A total of nine animals underwent surgery: three controls and six treatment animals. On each control animal four full thickness dermal incisions were made on the dorsum. The two anterior incisions were closed with uncoated 3-0 Vicryl and N-butyl-2-cyanoacrylate glue; the posterior incisions were closed with Vicryl alone. In the experimental animals four full thickness wounds were made on the dorsum; the two anterior incisions were closed uncoated Vicryl and a mixture of HF—Br and N-butyl-2-cyanoacrylate (0.5 cc of HF—Br was added to 0.5 cc of N-butyl cyanoacrylate glue) was applied topically to the closed wound. The two posterior wounds were closed with HF—Br coated 3-0 Vicryl. Two treatment animals and one control animal were then euthanized at 2, 6, and 12 weeks and soft tissue specimens were taken for analysis.

Figure 2:
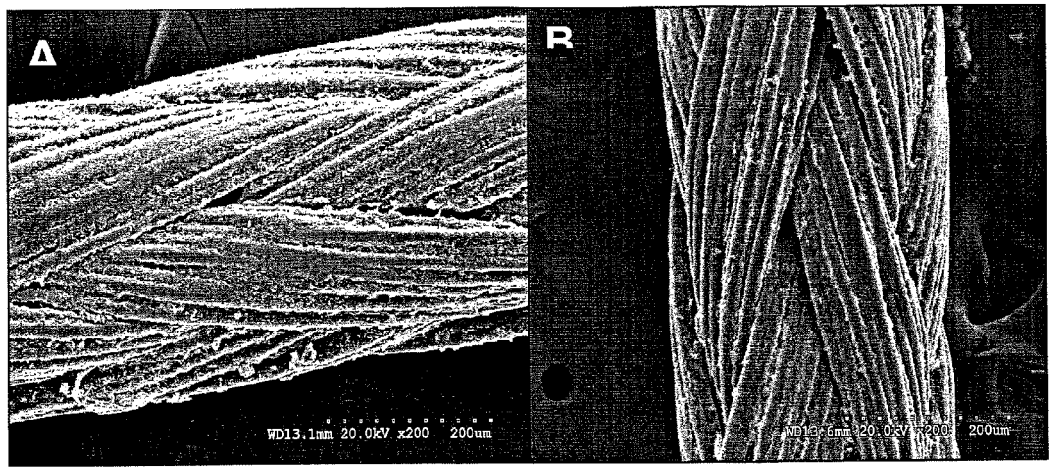

Suture Coating: 3-0 Vicryl absorbable sutures were weighed and placed in 1 ml serological pipettes. The pipettes were then filled with 1 cc of Halocur™ Halofuginone Bromide 0.5 mg/ml (Halocur® (Oral Halofuginone. 0.5 mg/mL) from Intervet International BV of Norway) and frozen at −80° C. for 24 hours and lyophilized. Pre and post coating weights were recorded and scanning electron microscopy (SEM) was used to show drug coating (particulate matter) on sutures (FIG. 2). Visual inspection of the coated sutures demonstrated a yellow coating, providing further evidence that the yellow Halocur had adhered.

Sutures were sterilized in ethylene oxide for surgical use. Weight recordings taken before and after coating showed an average of 96 µg/cm of drug on coated sutures.

Figure 3:
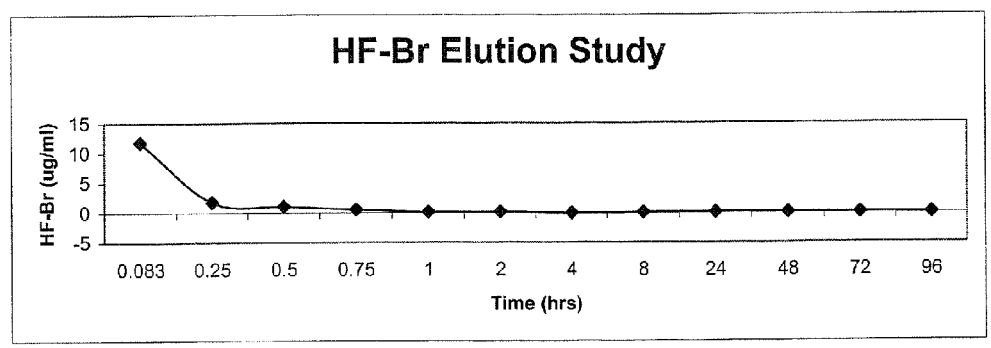
FIG. 3. Elution of HF—Br in vitro shows rapid drug release detected by UV spectroscopy at 243 nm.

To determine halofuginone elution, an in vitro elution study was performed. The release of halofuginone from coated Vicryl sutures into phosphate buffered saline (PBS) was used to estimate kinetics of drug release in vivo. A 2.5 cm segment of HF—Br coated Vicryl was placed in 1.5 mL of PBS and incubated at 37° C. At 5, 15, 30, and 45 minutes and 1, 2, 4, 8, 24, 48, 72, and 96 hours the segment was transferred into a new 1.5 mL aliquot of PBS, and the amount of halofuginone from the previous aliquot was measured with UV spectrophotometry at 243 nm. Data from UV spectrophotometry indicated a rapid release of HF—Br into PBS in vitro (FIG. 3). It was approximated that 90% of the total drug mass was released in 30 minutes and that the drug was nearly eliminated in 2 hours.

Gross Appearance of Wounds: More erythema and induration were visible in control wounds at two weeks than HF—Br treated wounds (data not shown). No significant difference in appearance was visible at later time points.

Figure 4A:
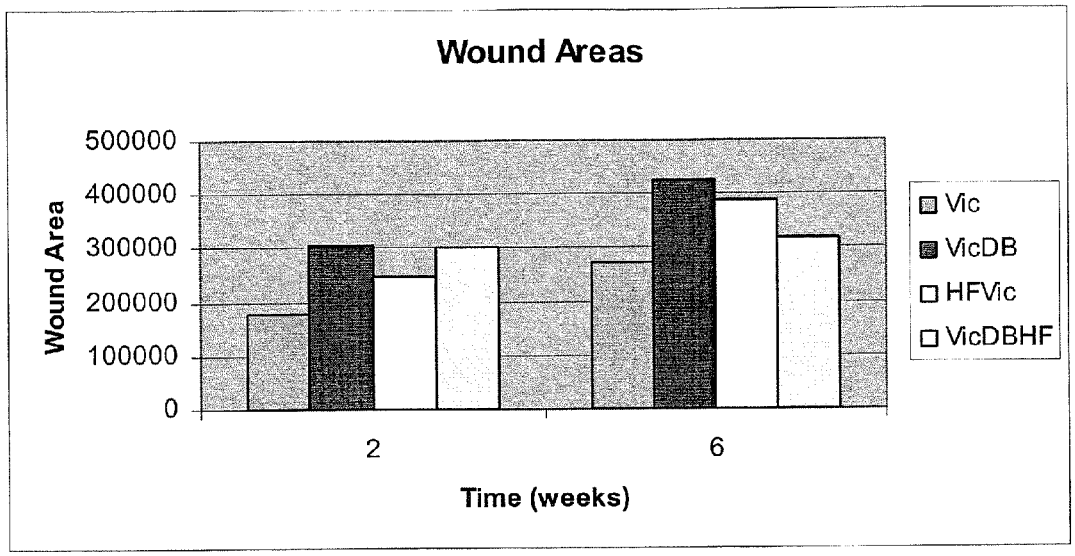
FIG. 4. Histology results. 4A: Wound Areas. 4B: Fibroblast Counts. Vic: uncoated 3-0 Vicryl suture. VicNBC: uncoated 3-0 Vicryl suture; then N-butyl-2-cyanoacrylate glue applied topically. HFVic: 3-0 Vicryl suture coated with halofuginone bromide. VicNBCHF: uncoated 3-0 Vicryl suture; then mixture of N-butyl-2-cyanoacrylate glue and halofuginone bromide applied topically. HF—Br: Halofuginone Bromide.
Figure 4B:
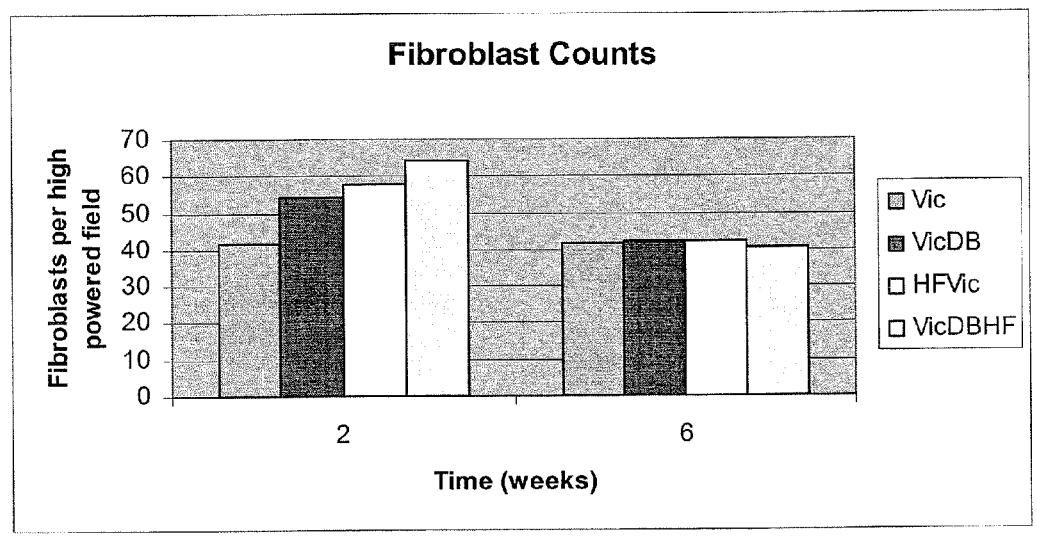

Soft tissue samples were harvested, embedded in paraffin and sectioned (5 µm). Sections were stained with Hematoxylin and Eosin (H&E) and Masson's Trichrome. Inflammation scores were recorded according to the method of Storch (*Surgical Infections*. 2002; 3: 89-98). The area of scar tissue deposition was approximated and calculated with light microscopy and a Zeiss™ digital image capture software system. Results are shown in FIG. 4.

Figure 5A:
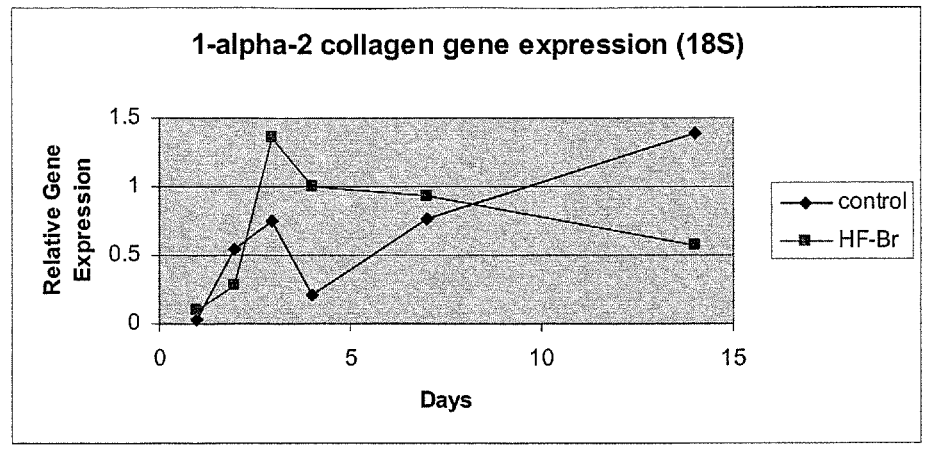
FIG. 5. Alpha 1 Collagen Gene Expression. Relative quantities of alpha 1 collagen gene expression were normalized with expression levels of 18S (5A) and GAPDH (5B) RNA. These values were then divided by the relative quantity of alpha 1 collagen gene expression in normal skin.
Figure 5B:
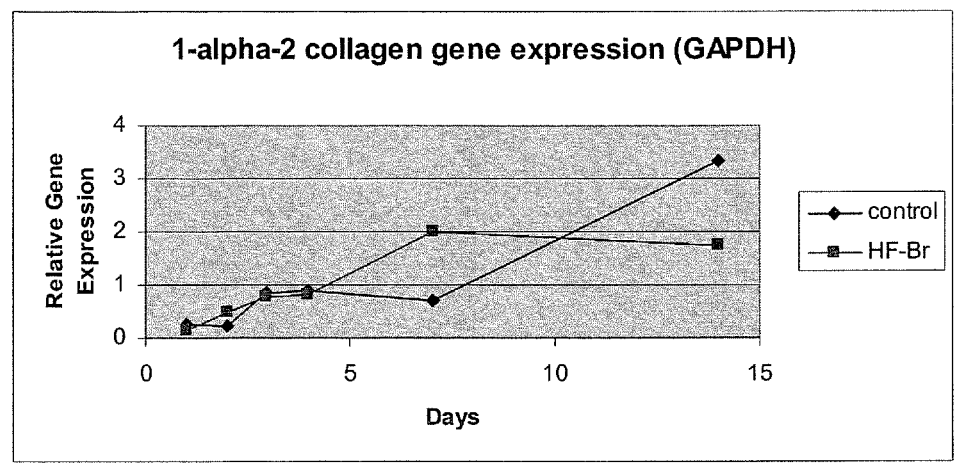

To determine alpha 1 collagen gene expression (in suture only animals), 2 mm punch biopsies of skin were taken at the border of wounds adjacent to suture material. Samples were flash frozen, pulverized, and RNA was extracted with Trizol reagent. Real time qPCR was employed to measure gene expression using rat 1-alpha-2 collagen ampliset. Relative quantities of alpha 1 collagen gene expression were normalized with expression levels of 18S and GAPDH RNA. These values were then divided by the relative quantity of alpha 1 collagen gene expression in normal skin. Results showed that 1-alpha-2 collagen gene expression is inhibited in wounds treated topically with HF (FIG. 5).

Figure 6:
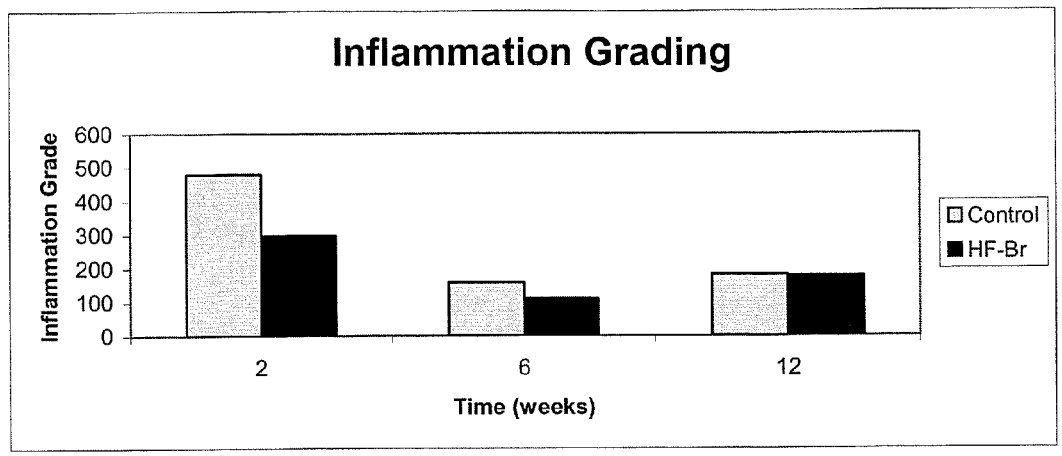
FIG. 6. Inflammation grading for weeks 2, 6 and 12.

The inflammatory response was visualized with H&E staining (not shown) and inflammation scores were consistently lower in HF—Br treated samples than in controls (FIG. 6). Masson's trichrome staining showed that cross sectional areas of collagen deposition (scar) were also consistently smaller in HF—Br treated samples than in controls (not shown).

Figure 7:
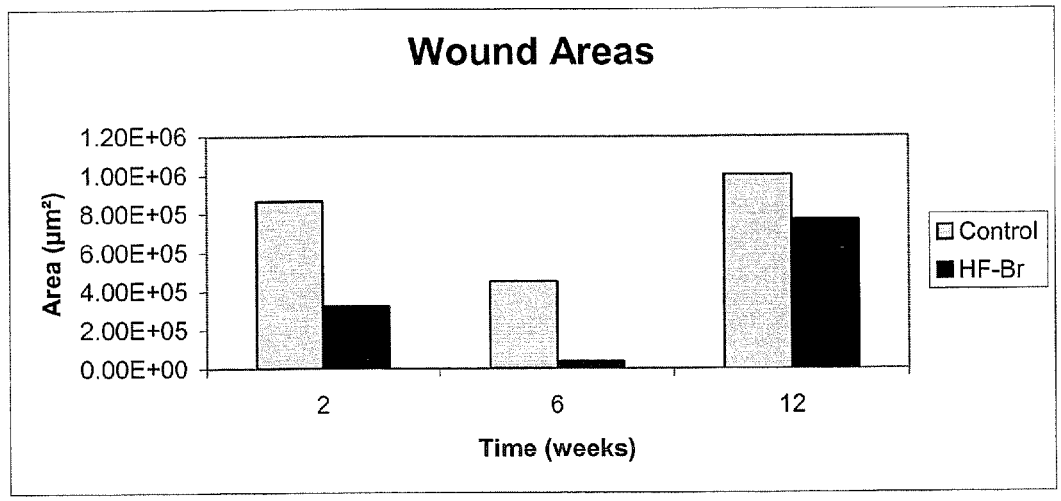
FIG. 7. Wound areas for weeks 2, 6 and 12.

Wound area approximations of Week 2 showed a 2.7 fold difference in collagen staining between HF—Br treated (322, 107 µm$^2$) and control (865,743 µm$^2$) (not shown). Wound areas for weeks 2, 6 and 12 are shown in FIG. 7.

Figure 8:
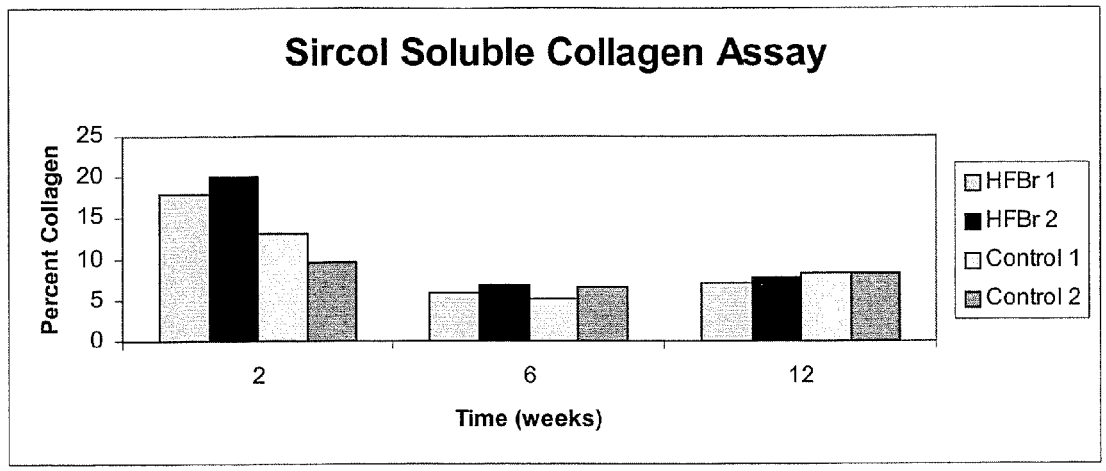
FIG. 8. Percent masses of salt soluble collagen in HF—Br treated and control wounds was determined by the Sircol™ Soluble Collagen Assay. Salt soluble collagen is representative of newly formed collagen.

To evaluate levels of newly formed collagen, tissue samples were digested in 1M NaCl in 0.05M Tris. Salt soluble collagen was then bound with a Sircol™ dye detection system and content was measured with UV spectrophotometry at 243 nM. Percent tissue masses of salt soluble collagen were higher in all week 2 samples. No significant difference in salt soluble collagen levels could be detected between HF—Br treated and control samples over each time point (FIG. 8).

Tensile strength of dermal wound tissue specimens is assessed by measuring the breaking point with a tensometer. Tissue specimens are harvested and analyzed immediately after animals are sacrificed. The specimens are attached to the tensometer and pressure is applied until the wound breaks. This breaking pressure is recorded as tensile strength.

Figure 9A:
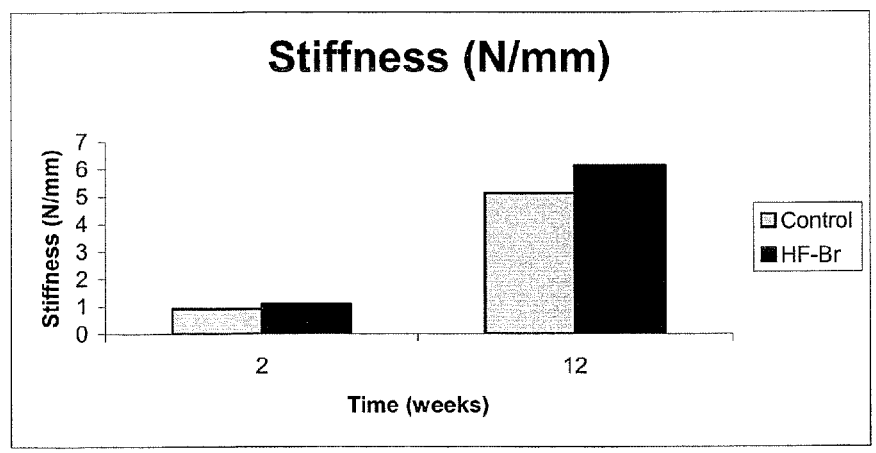
FIG. 9. Stiffness (9A), Ultimate Tensile Load (9B) and % Elongation (9C) of samples at 2 and 12 weeks.
Figure 9B:
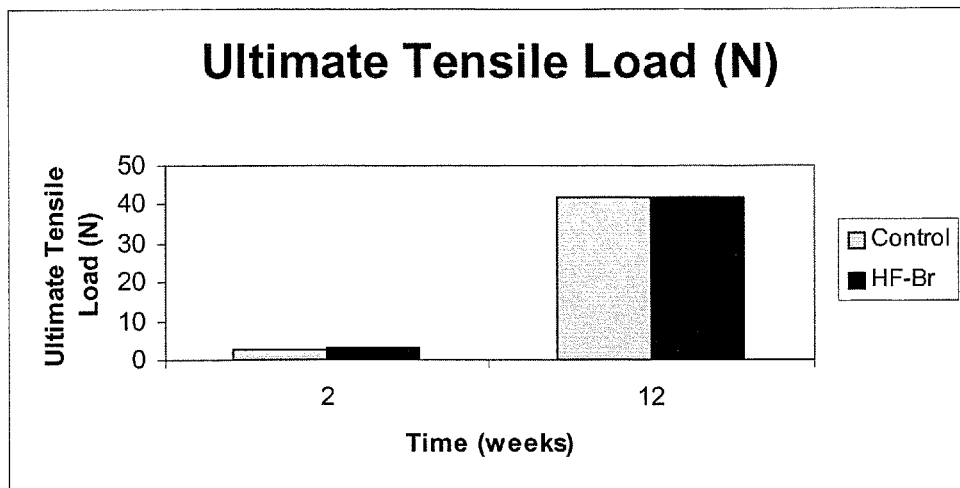
Figure 9C:
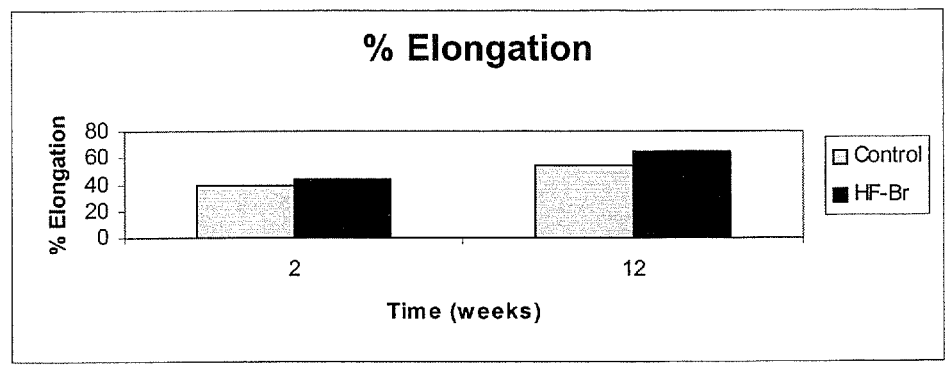

Skin samples were harvested so that the plane of the scar would be perpendicular to the direction of force applied. Samples were frozen, re-thawed, and secured by clamps in an tensometer (Instron™ Norwood, Mass.). Force was then applied until samples broke. Ultimate tensile load, percent elongation, and stiffness were then calculated for three control and three HF—Br treated samples at 2 and 12 weeks. Averages were reported. Average stiffness, ultimate tensile load, and percent elongation for all tissue samples increased from 2 to 12 weeks (FIG. 9). No significant difference was detected between treatment and control samples.

Conclusions: HF—Br coated suture delivers drug topically to dermal wounds, reducing scar tissue formation while maintaining tensile strength relative to control wounds. Type 1 Collagen content was the same in control and experimental wounds. HF can also be applied topically in the form of a cyanoacrylate based wound glue for effective wound closure.

Example 2

Paranasal Sinus Packing with Halofuginone

The ability of halofuginone bromide (HF—Br), an inhibitor of the alpha-1 collagen gene, to prevent scar tissue formation was examined in a rodent model of paranasal sinus surgery. Systemic administration of this compound has been found to inhibit scar tissue formation in animal and human studies, though none have examined its effects on scar tissue formation in sinonasal surgery. It was the objective of this study to determine if topical application of HF—Br will prevent scarring in an animal model of paranasal sinus surgery.

The potency of halofuginone bromide has led us to hypothesize that topical application in low doses would be more than sufficient to inhibit collagen type-1 production in an open wound and would have virtually no systemic risk of side effects. Based upon this hypothesis, we have compounded a formulation of halofuginone bromide that can be used topically as a packing material in the sinus to prevent post-operative scar tissue formation.

The use of rodent models in the study of paranasal sinus injury and wound healing has been established by previous studies in mice (Bomer et al. *Arch Otolaryngol Head Neck Surg*. 1998 November; 124(11):1227-32), but none have examined the role of halofuginone bromide in this context. We have developed a rat model of sinus surgery useful in the study of wound healing, in which micro CT evaluation and histological data confirmed removal of ethmoid tissue similar to that seen after sinus surgery in a human while sparing critical structures (data not shown).

Halofuginone is combined with a suitable material that will absorb blood and fluid to help with hemostasis and to act as a drug delivery vehicle. We have chosen a cellulose derivative for this purpose.

The packing materials were prepared as follows. step 1: prepare materials to desired size and shape for implantation. Cellulose sinus packing material (Merocel) was cut into 5 mm strips. step 2: prepare a solution of HFBr 0.5 µg/ml (Halocur® (Oral Halofuginone. 0.5 mg/mL), Intervet International BV of Norway). step 3: materials are then dipped and immediately frozen at −80 F for 24 hours. step 4: frozen materials are then lyophilized (vacuum dried). step 5: materials are sterilized using ethylene oxide or gamma irradiation. Visual inspection of the coated Merocel demonstrated a yellow coating, providing further evidence that the yellow Halocur had adhered.

Topical application of a halofuginone/cellulose derivative packing was tested for the prevention of scar tissue formation in the paranasal sinuses of a rat. The paired, anatomically identical paranasal sinuses of the rat allow one side to serve as a control and the other to serve as experimental. The control sinus was packed with an uncoated cellulose derivative packing material (Merocel). The other (experimental) sinus cavity was packed with a halofuginone bromide coated cellulose derivative compound packing material. A second set of animals underwent paranasal sinus surgery and no packing material of any kind was placed. Both packing preparations provide adequate homeostasis and require removal, as in the human clinical scenario. The surgical wound was closed using absorbable subcuticular sutures. Sinus surgery was performed in the rat and packs placed for 5 days. Sinus specimens were harvested and analyzed.

Table 1 below represents the weight of drug on the Merocel packs that were placed in the rat sinuses. Dry mass is weight of pack prior to coating with drug. Wet mass represents weight of pack after coating with drug. Drug mass represents total amount of drug applied as a coating to pack. This figure is calculated by subtracting dry mass from wet mass. Mean drug mass is the average of drug masses 1-10, with standard deviation as shown.

TABLE 1

Mass of HFBr-coated Cellulose Derivative (Merocel) Sinus Pack

| Pack | Dry Mass (g) | Wet Mass (g) | Drug Mass (g) |
| --- | --- | --- | --- |
| 1 | 0.0243 | 0.0301 | 0.0058 |
| 2 | 0.0244 | 0.0309 | 0.0065 |
| 3 | 0.0276 | 0.037 | 0.0094 |
| 4 | 0.0253 | 0.0326 | 0.0073 |
| 5 | 0.0245 | 0.0351 | 0.0106 |
| 6 | 0.0264 | 0.0344 | 0.008 |
| 7 | 0.0246 | 0.0315 | 0.0069 |
| 8 | 0.0282 | 0.0347 | 0.0065 |
| 9 | 0.0266 | 0.0344 | 0.0078 |
| 10 | 0.0274 | 0.0397 | 0.0123 |
| | | Mean Drug Mass (g) | 0.00811 |
| | | Standard Dev | 0.00201 |

Figure 10:
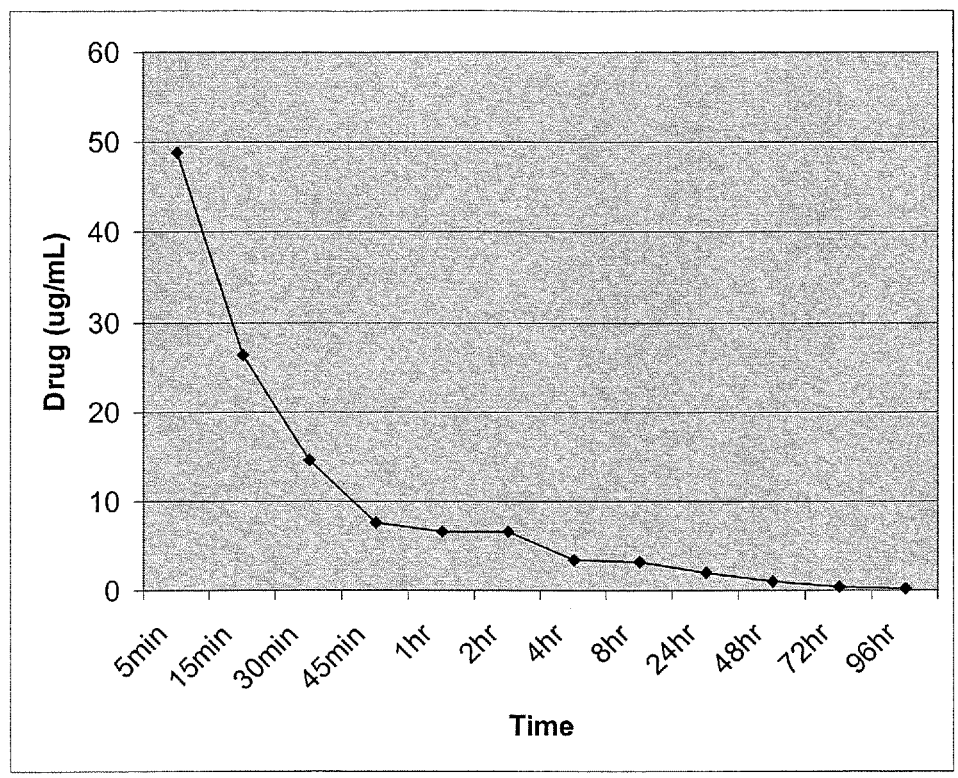
FIG. 10. Sinus Packing in vitro elution study. 80% of drug eluted in 1 hour.

Elution studies in vitro showed that 80% of the drug eluted in 1 hour (FIG. 10). In vivo elution studies were performed on packs removed 5 days post-operatively, placed in 10 mL PBS for 8 hrs, and 300 uL aliquot placed in spectrophotometer (blanked with a control pack removed post-operatively). No drug could be identified on post-op day 5 packing (not shown), suggesting that total amount of drug was given.

Figure 11:
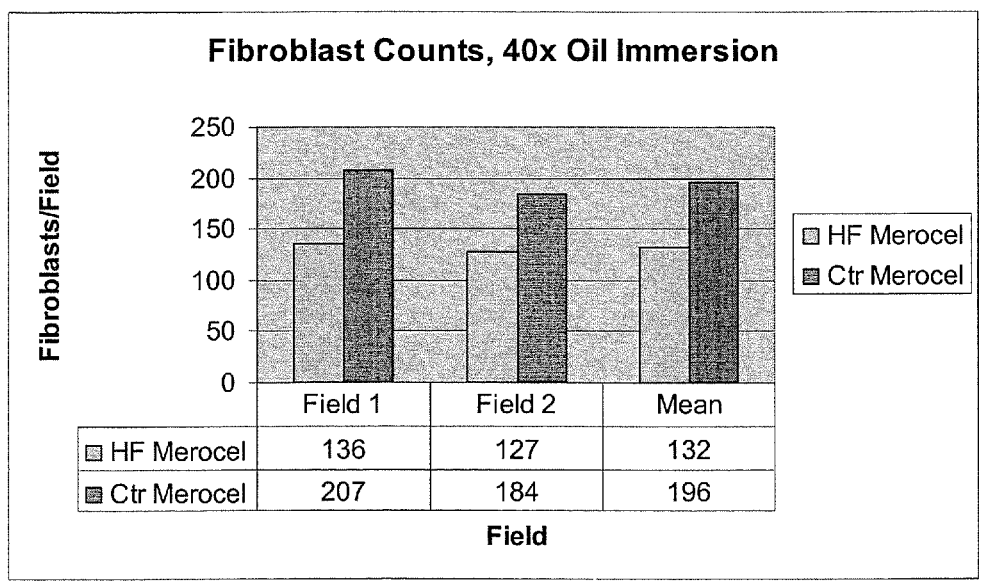
FIG. 11. Fibroblast Counts decreased in HF sinus pack wounds.

Fibroblast counts revealed decreased fibroblast counts in HF sinus pack wounds (FIG. 11). Collagen staining with Masson's trichrome staining showed decreased collagen staining in HF sinus pack wounds when compared to non-HF-coated cellulose pack (not shown).

Conclusions: Topical administration of HF—Br reduced post-operative scar formation in the paranasal sinus.

Example 3

Paranasal Sinus Packing Gel with Halofuginone or Mithramycin

An alternative to using a coated cellulose pack in the sinus is a sinus packing gel. This formulation was made by combining halofuginone (HF—Br) (Halocur® (Oral Halofuginone. 0.5 mg/mL), Intervet International BV of Norway) with carboxymethylcellulose (CMC) and storing as a dry sterile powder. The mixture was prepared, by weight with CMC (26.5%), halofuginone (0.00735%) and water (73.5%). This mixture achieved a workable viscosity for topical application. The mixture was lyophilized and pulverized to form a powder and then sterilized with gamma irradiation or ethylene oxide. The powder can then be reconstituted with sterile water to form a gel which is instilled in the sinus at the time of surgery for hemostasis and scar control.

Mithramycin in a liquid form is combined with a powder form of cellulose derivative to form an injectable gel. The mixture was prepared, by weight with CMC (9.9%), mithramycin (3.2%) and water (86.9%). This mixture achieved a workable viscosity for topical application. The mixture was lyophilized and pulverized to form a powder and then sterilized with gamma irradiation or ethylene oxide. At the time of rodent sinus surgery the gel is reconstituted with a suitable amount of water.

Topical application of mithramycin gel sinus packing was tested for the prevention of scar tissue formation in the paranasal sinuses of a rat. The paired, anatomically identical paranasal sinuses of the rat allow one side to serve as a control and the other to serve as experimental. Bilateral ethmoidectomy was performed. The control sinus was not packed The other (experimental) sinus cavity was packed with mithramycin gel containing 200 mcg of mithramycin (0.3 cc). Mithramycin gel preparation provided hemostasis. The surgical wound was closed using absorbable subcuticular sutures. Sinus specimens were harvested and analyzed at 2 and 6 weeks. All animals survived surgery with no adverse effect. When experimental (mithramycin gel) specimens were compared to controls, experimental animal showed less new collagen, less fibroblast infiltrate and regeneration of paranasal sinus epithelium. It can be concluded that a mithramycin gel paranasal sinus packing material is well tolerated at a drug dose of 200 mcg in a rat with reduction of scar tissue and re-epithelialization of the paranasal sinus cavity by 6 weeks.

Example 4

Treatment of Esophageal Stenosis with an Absorbable Drug Eluting Esophageal Stent Esophageal stenosis or stricture refers to narrowing of the esophagus secondary to the deposition of scar tissue in response to disruption of the epithelial lining. Pharyngoesophageal stenosis refers to stricture of the pharynx, hypopharyngeal and proximal esophageal segments. Deposition of scar tissue can occur secondary to gastroesophageal reflux disease (GERD), radiation or chemotherapy for cancer, surgery, trauma or inflammatory diseases. Contraction of this scar reduces the esophageal lumen, and can lead to the inability to swallow, inanition, aspiration and death (Ruigomez et al. *Am J Gastroenterol.* 2006; 101:2685-2692). When a tubular (luminal) structure is traumatized, the protective epithelial lining is disrupted and replaced by scar tissue that forms a circular scar. This circular scar contracts and reduces the luminal cross sectional area, which reduces flow through that structure.

Current treatments for luminal stricture conditions seek to stretch (dilate) and stent the involved segment of structured organ, to remove the involved segment of the organ, to bypass the involved organ or replace the organ entirely (organ transplant). The tissue trauma associated with these approaches inevitably leads to the formation of more scar tissue and an uninterrupted cycle of tissue trauma followed by scar tissue deposition, contraction and stenosis. Metallic stents have been used with limited success to try to resist contractile forces, but the chief drawback associated with this approach is that the stent causes continued tissue trauma that stimulates more collagen production and ultimately must be removed. For this reason, in some embodiments of the present invention, an absorbable stent is provided.

The gold standard, first line treatment for esophageal stricture disease has been endoscopic dilatation. Failure of such endoscopic procedures is common and necessitates a highly morbid open approach to remove the esophagus and reconstruct with gastric or free tissue transfer. The most common complication of either treatment is recurrence of stricture and need for repeat dilatation and stenting (Pereira-Lima et al. *Am J Gastroenterol.* 1999; 94:1497-1501).

Because of the poor success rate of operative approaches to esophageal stenosis, adjunctive surgical techniques have been employed to oppose the process of wound contraction and to prevent stricture recurrence. These methods include long term stenting with non-absorbable stents following stricture therapy as well as the local injection of various pharmacologic agents (corticosteroids, mitomycin C, colchicine, etc), in an effort to reduce the incidence of recurrence. None of these efforts have been successful and therefore a new treatment paradigm for dealing with this problem must be sought.

An absorbable esophageal stent is placed that administers topical collagen inhibitor after stricture lysis. These stents do not need to be removed, which minimizes risk to the patient. The drug eluting, absorbable esophageal stent will not only improve the treatment of esophageal stricture, but also have translational implications for treating other luminal strictures in anatomic sites such as the urethra, tracheobronchial tree, intestine, and blood vessels. There is evidence that orally administered or locally injected halofuginone can safely treat and prevent luminal stricture disease. Less is known about its effectiveness as a topical agent, but topical application is advantageous as it would deliver drug directly to tissue and it would avoid systemic doses which could interfere with systemic collagen homeostasis and blood coagulation. For example, in a recent Phase I clinical trial, systemic doses of 3.5 mg per day were associated with bleeding. Based upon this evidence, we believe that the ideal method of drug delivery would be topical on an absorbable, drug eluting stent in doses that would achieve molar concentrations in the range of $10^{-6}$ M and $10^{-9}$ M. Such a stent would administer drug directly to the area of injury with little or no systemic effect and the stent itself would be digested with no harmful effect.

Toward the goal of developing a bioabsorbable, non-drug eluting stent, investigators in Japan have recently showed promising results in a small human clinical trial in which an absorbable woven non-drug coated polylactic acid (PLA) stent was effective and safe for the treatment of benign esophageal stricture (Tanaka et al. *Digestion* 2006 October; 74:199-205).

We hypothesize that an absorbable HFBr (or other collagen inhibitor) coated esophageal stent will moderate scar tissue formation in a rat model of esophageal stricture formation, and we applied topical HF—Br in the form of an absorbable drug eluting esophageal stent in order to prevent cicatrization and luminal stenosis.

Previous animal models have used a caustic burn model (Sodium Hydroxide) to achieve esophageal injury. We were concerned that the pH of the esophagus would be sufficiently altered by sodium hydroxide so as to effectively alter the activity of a topical HFBr application and we therefore will use an electrocautery burn model.

Figure 12:
FIG. 12. A: Non-HFBr PLA implant (4×), B: HFBr electrospun implant (4×). Masson trichrome stain (blue is collagen). Note reduced thickness of collagen capsule (marked with arrows).

Electrospinning technology was used to make a poly(lactic-co-glycolic acid) (PLGA)/HFBr impregnated material that we have implanted subcutaneously in a rat. We found that this material was readily absorbed with reduced fibrous (scar) capsule formation (FIG. 12). Electrospinning uses an electrical charge to form a mat of fine fibers. The standard setup for electrospinning consists of a spinneret with a metallic needle, a syringe pump, a high-voltage power supply, and a grounded collector. A polymer, sol-gel, composite solution (in our case PLGA/HFBr melt solution) is loaded into the syringe and this liquid is driven to the needle tip by a syringe pump, forming a droplet at the tip. When a voltage is applied to the needle, the droplet is first stretched and then an electrified liquid jet is formed. The jet is then elongated and whipped continuously by electrostatic repulsion until it is deposited on the grounded collector. Whipping due to a bending instability in the electrified jet and concomitant evaporation of solvent allow this jet to be stretched to desired diameters.

For the esophageal stent we use this same procedure to spin a tubular structure that will have an outer diameter of 2.5-3 mm (the approximate diameter of an adult rat esophagus). We record the mass of PLGA used and control the amount of drug used (0.5 mg maximum based on human data (de Jonge et al. *Eur J Cancer.* 2006 August; 42(12):1768-74) and our existing experience with HFBr in rats). Once the stent is fabricated, we study the material using scanning electron microscopy to look for even distribution of PLGA and HFBr. We weigh and measure the length of each specimen and then perform drug elution studies in vitro as previously performed on paranasal sinus and suture materials. Briefly, we place the fabricated stent in PBS and measure drug levels using spectrophotometry at defined time points to establish a drug distribution (µg/ml) curve. Initially we measure time points of 5 min, 10 min, 20 min, 40 min, 60 min, 2 h, 4 h, 8 hr, 12 h 24 h 48 h 72 h and 96 h or until greater than 80% of drug has been released. These data allow us to estimate the amount of drug per unit length of stent or per $mm^2$ of stent surface area.

The rat model described above is used to test our hypothesis that topical collagen inhibitor will inhibit scar tissue formation in the esophagus. Three groups of animals are used: Group 1 is normal rats, Group 2 is caustic esophageal injury without stent placement and Group 3 is caustic esophageal injury with PLGA/HFBr stent placement. All animals undergo pre-operative weight, esophagram and serum blood draws for drug (HFBr) levels.

Animals in Groups 2 and 3 undergo surgery. In Group 3, the prefabricated stent is inserted through a small esophagotomy incision just distal to the burn injury at the time of burn injury and is secured with a single 6.0 monocryl suture to assure that the stent remains at the site of injury. The esophagotomy incision is closed with an interrupted absorbable suture. Wounds are closed in a standard fashion with absorbable suture, and animals are awakened and allowed to recover. In Group 3, 5 animals are euthanized at days 1, 2, 3, 4 and 5 for transcardiac serum blood draw to measure systemic levels of HFBr. In these same animals, the esophagus is opened and gross evaluation for stent integrity will be carried out. At 2, 6, 12 and 24 weeks remaining animals in all groups are weighed, euthanized and esophagram is performed. Esophageal specimens are harvested fixed in formalin, embedded in paraffin, sectioned and stained with hematoxylin and eosin and Masson's trichrome. We quantify the amount of scar tissue deposition using light microscopy and digital technology to measure scar areas. Real time PCR measurements are performed to quantify the activity of the Type-1α collagen activity. Pre and post weights are used as a marker of swallowing functionality and are compared across groups.

Example 5

Treatment of Abdominal Adhesions in a Rat Model

During surgery on large body cavities such as the abdomen, scar tissue forms and causes vital organs in that cavity to stick together in a process called adhesion formation. These adhesions cause loss of normal organ function and can lead to chronic pain and death. Prevention of adhesion formation would improve outcomes after surgery. Therefore one or more collagen inhibitors are topically applied to internal organs during or post surgery.

Adhesions are created in the abdominal cavity of animals are treated with a collagen inhibitor (e.g., halofuginone bromide) that blocks scar tissue formation. The drug is placed directly in the abdominal cavity by implanting an absorbable material or non-absorbable mesh in order to prevent adhesion formation between vital organs after surgery. The abdominal cavity is surgically opened and adhesions are created by gently rubbing the vital organs with a gauze sponge. Halofuginone bromide-coated absorbable hemostatic material is then applied directly into the abdominal cavity and the wounds are sewn shut.

The rat is used as the animal model. Experimental models for abdominal adhesion formation are well described in the rat and all incorporate ventral midline incisions. One incision is made on the abdomen of each rat and then a visceral abrasion is created to mimic human surgery. Separate control and experimental rats are used. In each experimental animal, a HF—Br coated absorbable material is implanted. In each control animal a non-HF—Br coated absorbable material is implanted. In a third control group no absorbable material is implanted. At 2, 6, 12 and 24 weeks, animals are euthanized, the amount of adhesion formation is quantified by percent area of adhesion formed in the abdominal wall, and the gross appearance of the adhesions is evaluated. Soft tissue specimens are harvested and analyzed for adhesion formation using hematoxylin and eosin staining, Masson's Trichrome staining and collagen content assay. Tensile strength of the abdominal wall is also measured at 12 weeks. On days 1, 2, 3, and 4, one rat from each experimental group is euthanized for intracardiac blood drawing to access plasma levels of HF—Br.

We have coated oxycellulose with HF—Br (not shown), and this is used as the packing material for the abdominal adhesion.

Example 6

Catheter Coating

The following is a list of ureteral and urethral catheter material that we have demonstrated the ability to coat with halofuginone using imaging studies (microscopic and gross), weight changes, and elution data over 4 days:

General device material: Silicone, Silastic, Latex, Polyurethane, Nitinol, PLGA.

Boston Scientific products: Percuflex stents, Flexima stents, Pebax material.

Cook stents: Polyurethane, Sof-flex, AQ stents, Endo-sof stents.

Bard stents: Polyurethane, Latex, Woven stents, Lubricath Foley, Inlay stent, Elastomer coated catheters, Silver coated catheters.

The stents were coated as follows: 1. Wet stent with PBS and cover with PBS soaked gauze and microwave for 40 sec; 2. Dip stent in 2% PLGA-COOH to cool; 3. Dry under hood; 4. Cover with PBS soaked gauze and microwave (or plasma) for 30 sec; 5. Coat stent with halofuginone (immerse) and freeze in liquid nitrogen and lyophilize overnight; 6. Weight should be measured before and after coating to estimate drug content.

Stents and other substrates made of the same materials (e.g., esophageal and tracheal products) are coated in the same fashion.

Example 7

PLGA Sheets, Uncoated Versus Coated with Halofuginone

Figure 13:
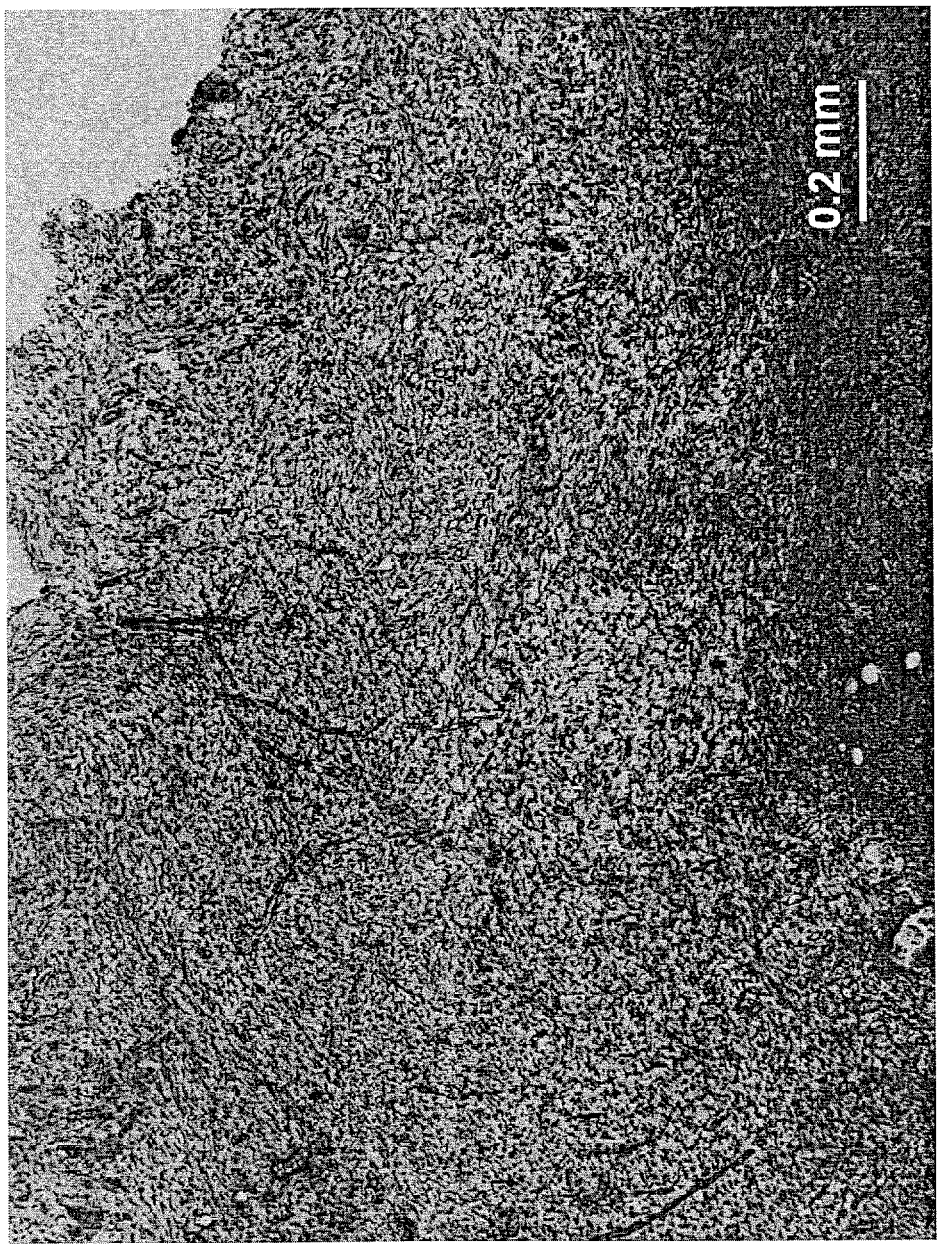
FIG. 13. Halofuginone coated PLGA was placed subcutaneously in the rat model. The PLGA has completely dissolved and there is no new collagen, but hemorrhage and inflammation.
Figure 14:
FIG. 14. Uncoated PLGA is still present and surrounded by a collagen capsule.

The ability of collagen inhibitor coated biodegradable products to prevent scar is demonstrated. FIG. 13: halofuginone coated PLGA was placed subcutaneously in the rat model. The PLGA has completely dissolved and there is no new collagen, but hemorrhage and inflammation. FIG. 14: uncoated PLGA is still present and surrounded by a collagen capsule.

Example 8

Collagen Inhibitor Coated Silicone Disks in Rats Subcutaneous Tissue

Figure 15:
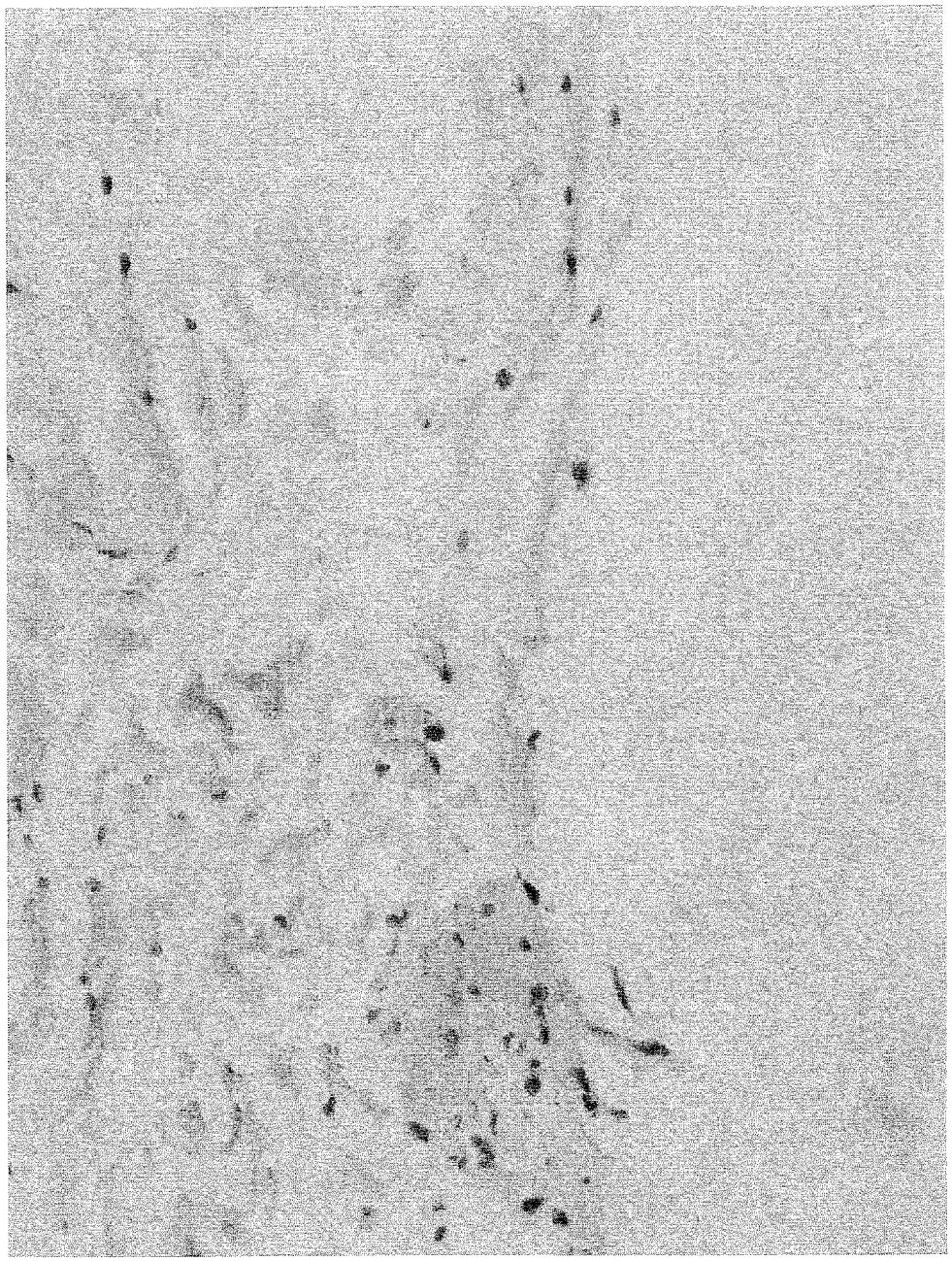
FIG. 15. Silicone discs coated with halofuginone have a paucity of new collagen surrounding the subcutaneous implantation site at two weeks in the rat model.
Figure 16:
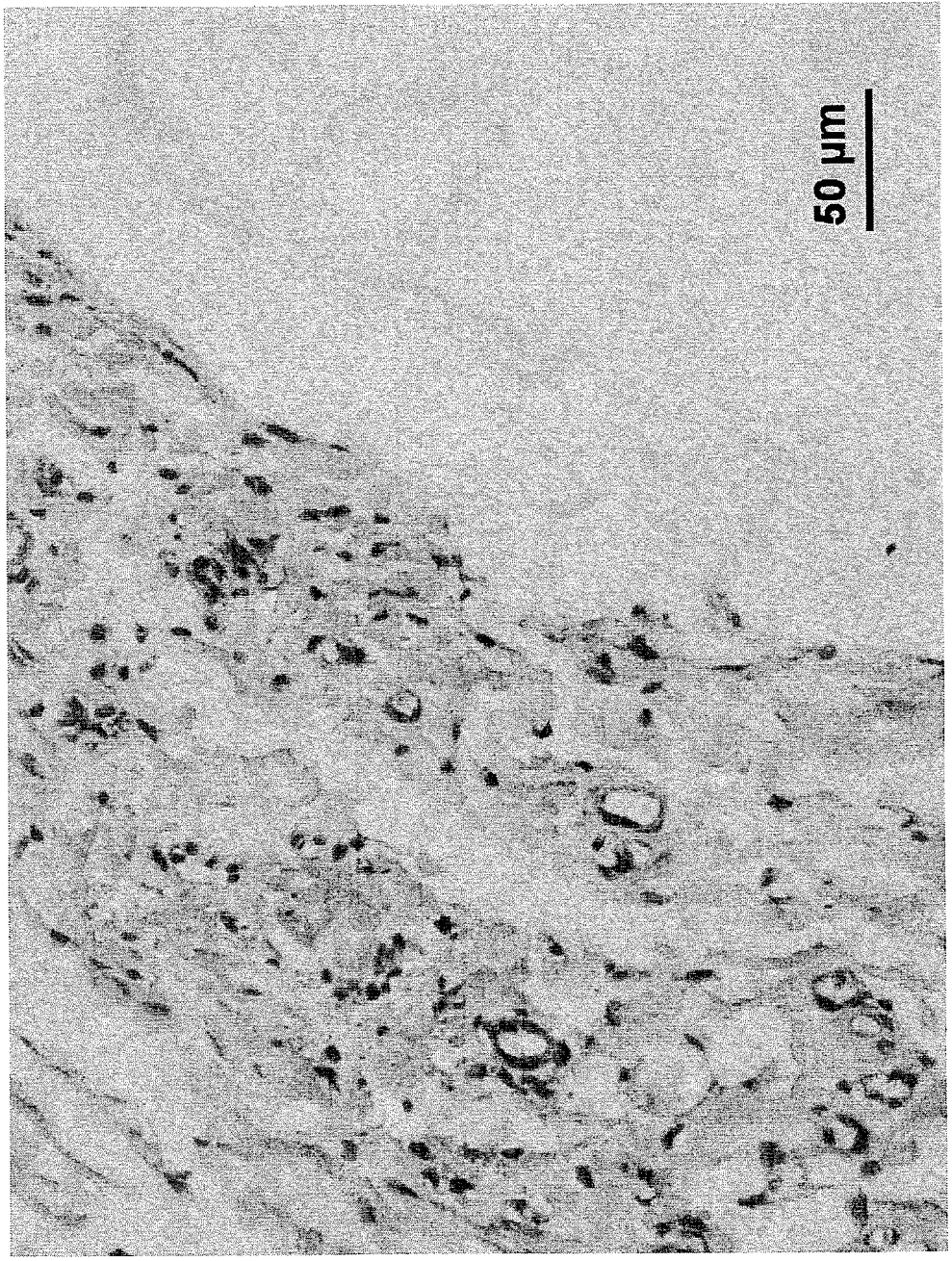
FIG. 16. Uncoated silicone disks show significantly more collagen surrounding the implantation site.

The following data represents the ability of collagen inhibitor (halofuginone) coated silicone disks to prevent capsule formation. FIG. 15: silicone discs coated with halofuginone have a paucity of new collagen surrounding the subcutaneous implantation site at two weeks in the rat model. FIG. 16: uncoated silicone disks show significantly more collagen surrounding the implantation site.

Example 9

Bioabsorbable Mithramycin-PLGA Tracheal Stents for the Treatment of Tracheal Stenosis Tracheal stenosis is a clinical condition in which the trachea is narrowed due to trauma, surgery, radiation, tumor and other inflammatory conditions. It affects an estimated 10% of patients undergoing endotracheal intubation in the United States every year (Lalwani, A. "Tracheal Stenosis." *Current Diagnosis & Treatment in Otolaryngology Head & Neck Surgery, 2nd Edition*. McGraw-Hill: New York, 2008). In 2004, over 500,000 intubations were performed on adults in short stay hospitals (Kozak et al. "National Hospital Discharge Survey: 2004 Annual summary with detailed diagnosis and procedure data." National Center for Health Statistics. Vital Health Stat 13(162), 2006) and with each intubation there is a chance of trauma to the trachea that could lead to scar tissue formation. Premature infants and critically ill patients may remain intubated for extended periods of time leading to tracheal trauma, scar tissue formation and narrowing of the tracheal airway. The deposition of scar tissue in the trachea leads to organ dysfunction, airway narrowing (stenosis), difficulty breathing, airway obstruction, decreased quality of life and even death.

The process of scar tissue formation in the trachea begins with a traumatic event followed by the deposition of collagen at the site of injury. Over time, the collagen fibers contract circumferentially leading to narrowing (stenosis) of the trachea. Current methods for treating tracheal stenosis include dilation (stretching) and stent placement to maintain luminal integrity. Unfortunately, the trauma of dilation leads to the formation of more scar tissue setting up an endless cycle of trauma followed by cicatrization that ultimately leads to failure. In all cases, the stents that are placed to maintain the tracheal airway are permanent and usually exhibit mechanical failure, extrusion or obstruction. Ideal management of tracheal stenosis would employ dilation and application of an absorbable stent that would elute a pharmacologic agent that prevents the deposition of type $1\alpha$ collagen at the site of injury. The purpose of this experiment was to study the effect of topical application of a type-$1\alpha$ collagen inhibitor on the formation of tracheal stenosis in an animal model.

Tracheal stenosis is defined as narrowing of the trachea. Even small decreases in the diameter of the airway will lead to significant reductions in airflow in the trachea as dictated by Poiseulle's Law, which states that the resistance to laminar flow is inversely proportional to the fourth power of the radius of the tube. Therefore, reduction in tracheal cross sectional area works to exponentially increase the resistance to airflow. The stenosis may be caused by surgery, trauma, chronic inflammatory disease, neoplasm, or collagen vascular disease. Of these causes, trauma in the form of postintubation injury is the most common cause of benign tracheal stenosis. Postintubation stenosis is estimated to occur in 8-13% of all cases involving assisted ventilation (Lalwani, A. "Tracheal Stenosis." *Current Diagnosis & Treatment in Otolaryngology—Head & Neck Surgery, 2nd Edition*. McGraw-Hill: New York, 2008).

Due to the vast number of intubations that occur in the United States, this complication is unfortunately all too common. Despite the magnitude and severity of the problem, there is no cure for tracheal stenosis once it develops. Dilation, laser resection and stenting are standard treatments that do not work due to reformation of scar tissue, stent migration, stent failure, or stent erosion (Montgomery, "T-tube tracheal stent." *Arch. Otolaryngo*. 1965, 82: 320-21; Wu et al. "Airway stents in Management of tracheal Stenosis: have we improved?" *ANZ Journal of Surgery*. 2007, 77: 27-32; Preciado et al. "Laryngeal and tracheal stents in children." *Current Opinion in Otolaryngology & Head and Neck Surgery*. 2008, 16: 83-85; Rousseau et al. "Self-expandable prostheses in the tracheobronchial tree." *Radiology*. 1993, 188: 199-203; Remacle et al. "Progressive experience in tracheal stenting with self-expandable stents." *European Archives of Oto-Rhino-Laryngology*. 2002, 260: 369-73; Madden et al. "Do expandable metallic airway stents have a role in the management of patients with benign tracheobronchial disease?" *Annals of Thoracic Surgery*. 2006, 82: 274-78).

Surgical resection of the stenotic segment of trachea is limited to short segment stenoses, and even then fails in many cases or is complicated by permanent injury to the voice box (Grillo et al. "Management of congenital tracheal stenosis by means of slide tracheoplasty or resection and reconstruction, with long-term follow-up of growth after slide tracheoplasty." *Journal of Thoracic and Cardiovascular Surgery*. 2002; 123 (1): 145-152).

Biodegradable tracheal stents were fabricated by electrospinning using 15 w/v % poly(lactide-co-glycolide) (PLGA, molecular weight: 71 kDa, Lakeshore Biomaterials, Birmingham, Ala.) in 1,1,1,3,3,3-hexafluoro-2-propanol (99+%) (HFP, Sigma Chemical Co., St. Louis Mo.). 0.5 w/v % mithramycin was added to PLGA solution prior to electrospinning. The electrospinning set-up included a syringe pump, a high voltage supply, and a rotating mandrel (Custom Design & Fabrication, Richmond, Va.) to collect the fibers. A positive voltage (25 kV) was applied to the PLGA solution by the power supply (Spellman High Voltage, Hauppauge, N.Y.). The PLGA solution was delivered through an 18 gauge blunt tip syringe needle at a constant flow rate of 3 mL/hr using a syringe pump (Medfusion 2001, Medex, Inc., Carlsbad, Calif.). The collecting mandrel was a stainless steel rod (1.8 mm diameter). The distance between the syringe tip and the mandrel was 10 cm and the rotation rate was 1000 rpm. Stents made from PLGA without drug were used as a control, and these were fabricated using the same procedure.

A single long tubular stent with an internal diameter (ID) of 1.25 mm and an outer diameter (OD) of 2.25 mm was made from PLGA-only or MMA-PLGA The resulting single, long stents were then cut into 5 mm long segments for in-vivo implantation. Gross inspection, scanning electron microscopy (SEM) and drug elution analyses were performed in-vitro on all stent materials. Drug elution was performed by placing specimens in PBS on a shaker at 37° C. 500 mcl specimens of solution were drawn off systematically from 30 minutes to 120 h. Specimens were transferred into fresh PBS solution at each time interval. Stent degradation was observed grossly.

Adult Sprague Dawley rats were used for the experimental model. Animals were divided into four groups: Normal (Group A) tracheotomy only (Group B), tracheotomy with PLGA stent placement (Group C) and tracheotomy with MMA-PLGA stent placement (Group D). Group A animals underwent general anesthesia and were euthanized and the larynx, trachea and lungs were harvested for gross and histologic analysis. Group B, C, D animals underwent open tracheotomy through a vertical incision. In non-stent animals (Group B) the tracheotomy was closed primarily with 5.0 vicryl suture. In Group C and D animals stents were placed and no sutures were used to close tracheotomy site. Group D animals were sacrificed at POD 5 and 14 and tissue specimens collected. Group B and C animals were sacrificed and tissue specimens were collected at day 14.

Figure 17:
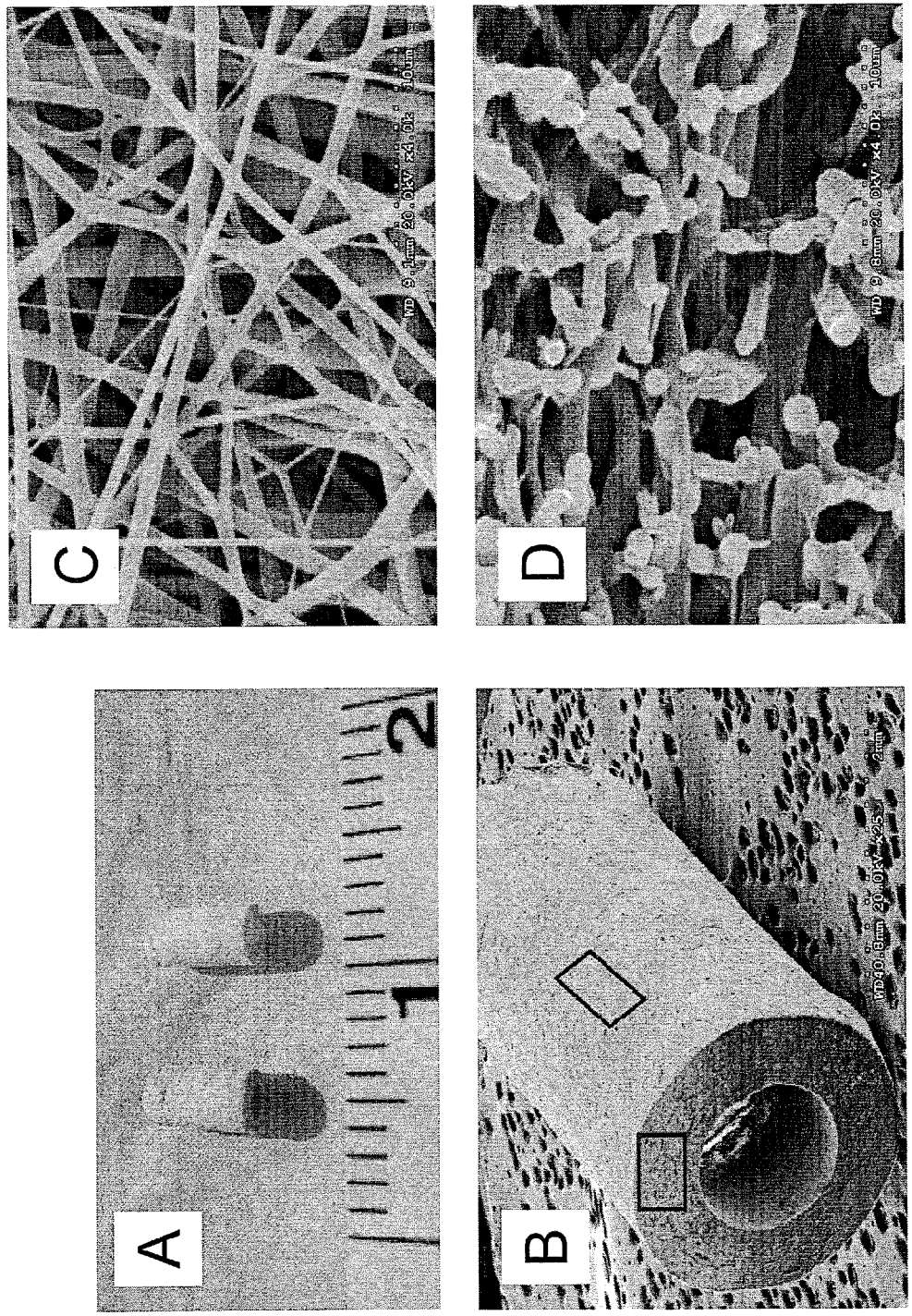
FIG. 17. MMA-PLGA (left) and PLGA (right) absorbable tracheal stents (A). Scanning electron microscopy (B-D) showing electrospun surface view (C) and crossectional view (D).

Upon gross inspection, fabricated PLGA and MMA-PLGA stents showed a uniformly round, smooth hollow tube of specified dimensions with no significant surface irregularities. MMA-PLGA fabricated stents displayed a uniform yellow color indicative of the presence of MMA drug within the stent material (FIG. 17A).

To confirm even incorporation of drug into the stent SEM (FIG. 17B) was carried out of the surface (FIG. 17C) and cross-sectional (FIG. 17D) aspects of PLGA and MMA-PLGA stents. No significant difference could be seen between the surface or cross-sectional appearances of the PLGA and MMA-PLGA stents.

Fabricated MMA-PLGA stents were tested in vitro to determine if drug would elute from the stent. When stents were placed in PBS solution MMA-PLGA stents fell to the bottom of the solution by 30 minutes suggesting ready water absorption due to presence of hydrophilic drug. UV spectrophotometry identified steady release of microgram quantities of drug into solution over a 152 hour time period. The concentration of drug in solution ranged from $1.48 \times 10^{-6}$ M to $2.9 \times 10^{-5}$ M Fabricated PLGA and MMA-PLGA stents were placed in PBS solution at 37° C. Solutions were changed every 24 hours and degree and manner of stent degradation were recorded. Steady dissolution of MMA-PLGA stents into solution without fragmentation was observed over a 90 day period.

Adult Sprague Dawley rats were used for the experimental model. Animals were divided into four groups: Normal (Group A) tracheotomy only (Group B), tracheotomy with PLGA stent placement (Group C) and tracheotomy with MMA-PLGA stent placement (Group D). Group A animals underwent general anesthesia and were euthanized and the larynx, trachea and lungs were harvested for gross and histologic analysis. Group B, C, D animals underwent open tracheotomy through a vertical incision. In non-stent animals (Group B) the tracheotomy was closed primarily with 5.0 vicryl suture. In Group C and D animals stents were placed and no sutures were used to close tracheotomy site. Group D animals were sacrificed at POD 5 and 14 and tissue specimens collected. Group B and C animals were sacrificed and tissue specimens were collected at day 14.

Figure 18:
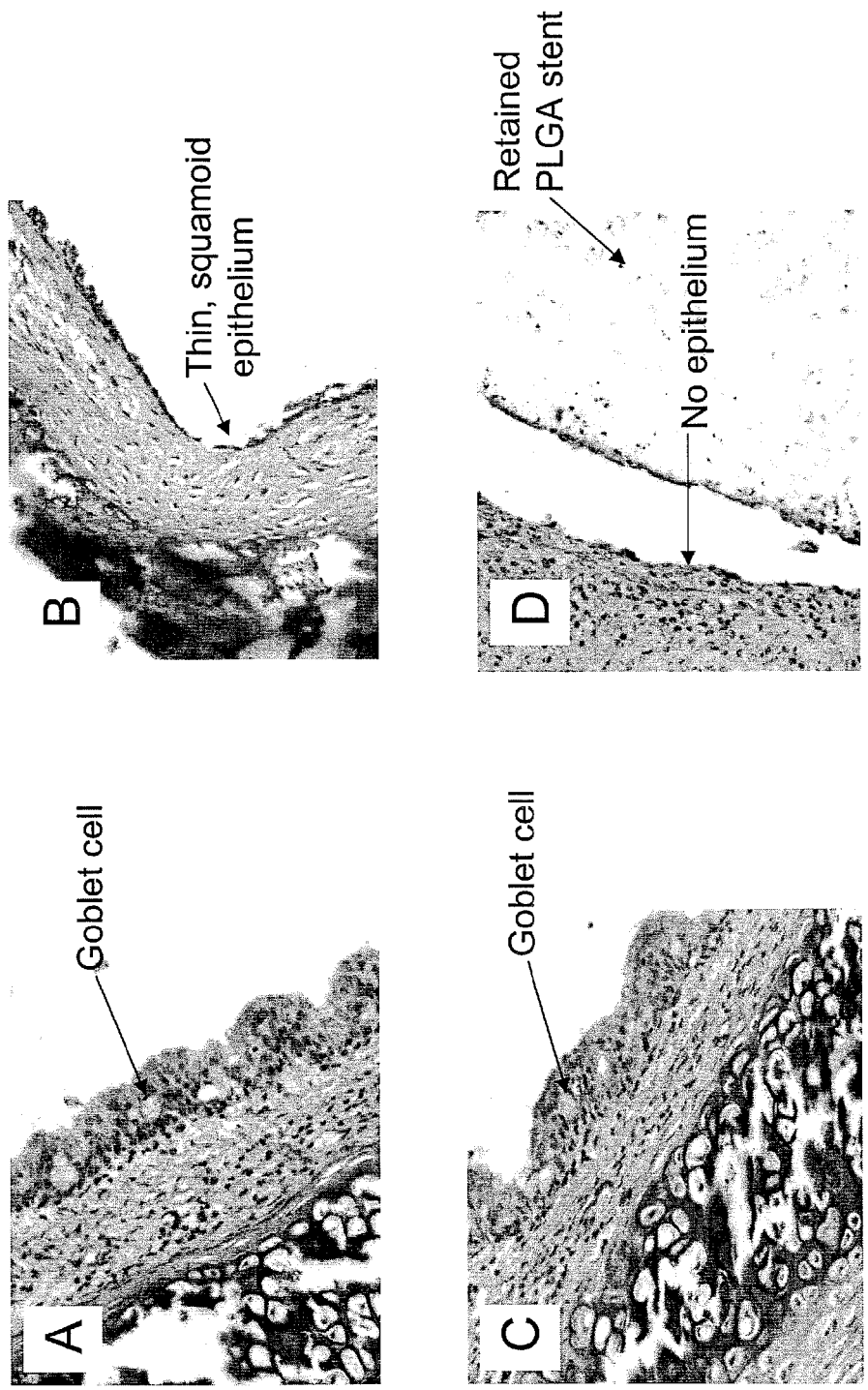
FIG. 18. A: Normal Rat Tracheal Respiratory Epithelium, 20×. B: Tracheotomy only, 20×. C: MMA-PLGA normal appearing regenerated tracheal respiratory epithelium, 20×. D: PLGA rat trachea, 20×. MMA-PLGA stent healing (C) shows normal regeneration of pseudostratified, columnar, ciliated respiratory epithelium with goblet cells when compared to normal (A), tracheotomy only (B) and PLGA (D) animals at 14 days.

Trachea Results:

Group A: No surgery. Hyaline cartilage lined by a pseudostratified, ciliated respiratory epithelium with goblet cells was demonstrated in all normal (Group A) animals. (FIG. 18A).

Group B: Rats undergoing tracheotomy-only showed deposition of scar tissue on H&E and Masson's trichrome staining at the site of tracheotomy. A thin flat squamoid appearing mucosal lining developed at the tracheotomy site; no normal respiratory epithelium could be identified (FIG. 18B). All animals survived surgery without acute airway obstruction.

Group C: Animals underwent PLGA stent placement. These animals developed scar tissue at the site of tracheotomy with intense inflammatory infiltrate (fibroblasts) and no evidence of a mucosal lining epithelium. Stent material was retained and maintained shape and structure at 14 days (FIG. 18C) All animals survived surgery without acute airway obstruction.

Figure 19:
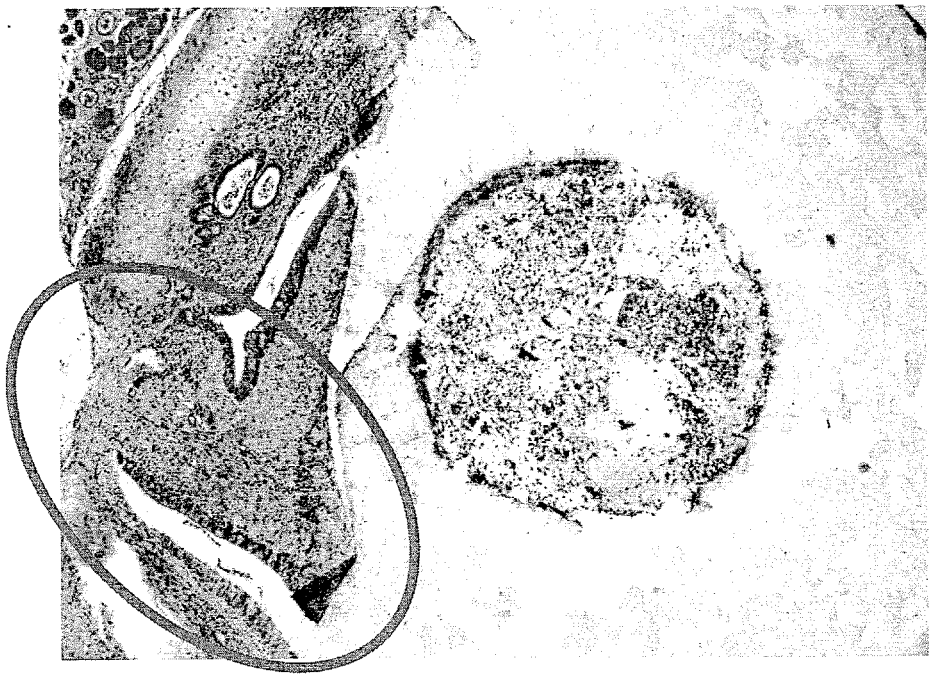
FIG. 19. Animals with MMA-PLGA tracheal stents showed less scar tissue formation when compared to PLGA-only stents (Masson's Trichrome, 4×).
Figure 19:
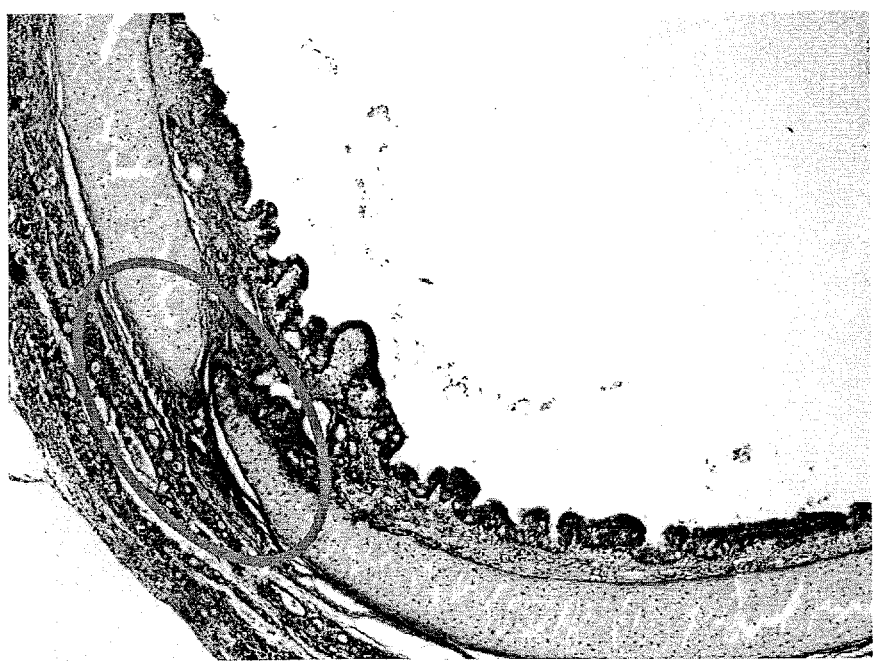

Group D: Animals underwent MMA-PLGA stent placement. Scar tissue deposition was reduced and all animals showed normal appearing pseudostratified, ciliated respiratory epithelium with goblet cells at the site of injury (re-epithelialization). No luminal stent material could be identified at Day 5 or Day 14 (FIG. 18D). All animals survived surgery without acute airway obstruction, In summary, scar deposition was decreased in MMA-PLGA treated animals when compared to MMA-PLGA treated animals (FIG. 19). All animals treated with MMA-PLGA stents developed normal appearing pseudostratified, ciliated respiratory epithelium with goblet cells at site of injury (re-epithelialization). PLGA-only animals did not re-epithelialize at all. Animals with tracheotomy only developed a squamoid mucosal lining.

Figure 20:
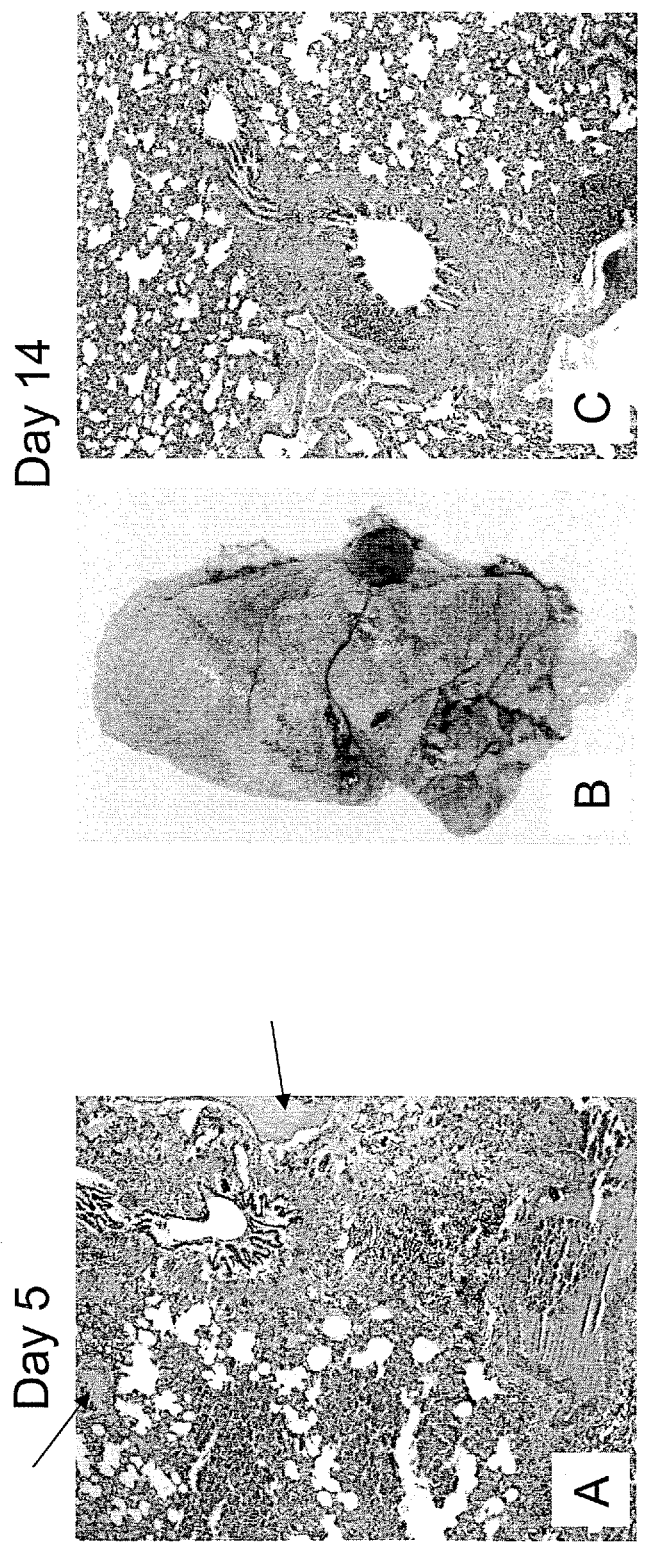
FIG. 20. Lung. Day 5 (A) shows retained MMA-PLGA stent material (arrows), peribronchiolar inflammation, edema and alveolar hemorrhage (20×). Day 14 shows healthy appearing lung, grossly (B) with (C) peribronchiolar lymphocytic inflammation, normal alveolar sacs and no retained stent material (20×).

Gross analysis of larynx, trachea and lung tissue revealed no abnormalities. No histologic abnormalities could be identified in the larynx. Lung tissue in MMA-PLGA specimens was characterized by varying amounts of hemorrhage, edema, rare peribronchiolar lymphocytic infiltrate and normal alveolar sac structure. Retained stent material was observed in Day 5 specimens but not in Day 14 specimens (FIG. 20).

In conclusion, these results demonstrate that MMA-PLGA bioabsorbable tracheal stents are feasible in a rodent model of tracheal stenosis. Functional MMA-PLGA bioabsorbable tracheal stents can be fabricated using an electrospinning technique with even drug distribution throughout the material, steady drug release in-vitro and in-vivo drug activity. The MMA-PLGA tracheal stents showed no adverse tissue effects in-vivo and evidence of favorable bioabsorption by complete absence of stent material at 5 and 14 days. Bioabsorbable MMA-PLGA tracheal stents were able to support airway patency prior to dissolution of stent material without any animal deaths, and showed decreased scar tissue formation at the tracheotomy site. Bioabsorbable MMA-PLGA tracheal stents supported re-epithelialization of tracheotomy wound sites with normal tracheal respiratory epithelium when compared to controls.

Example 10

Mithramycin a Topical Ointment for Prevention of Scar Tissue in Human and Rat Skin Wounds It was determined if a topical MMA ointment could be fabricated and applied safely to dermal wounds to ameliorate scar tissue formation.

A topical preparation was made by first preparing a water soluble base by melting a weight based mixture of polyethylene glycol (PEG) 400 (60%) and polyethylene glycol 3350 (40%) on a hotplate. The mixture was warmed to 65° C. and then removed from the hotplate and stirred until it became congealed. The resulting ointment base was placed in a sealed container and allowed to harden overnight at room temperature. Mithramycin-A powder in a ratio of 1:1,000 drug:base was then placed in a few drops of sterile water and mixed into the ointment base until a smooth, consistent yellow color was achieved throughout the ointment. The ointment preparation was then placed in a sealed container and stored at −20° C. The resulting ointment created was 0.1% MMA in a water soluble base. The ointment was essentially odorless and maintained its coloration over an 8 week period at −4° C. prior to discard. The ointment was easily applied with a 5 mL syringe.

A transdermal patch was created on a single human volunteer in order to apply MMA ointment to human skin. 500 mcg MMA was applied to the hairless skin of the forearm and a wax paper patch was placed over the ointment and taped into place with clear plastic tape. Every 24 h, the ointment was removed and re-applied for a total of 5 days. When 500 mcg of 0.1% MMA ointment (0.75 mg MMA/cc) was applied daily via a transdermal patch system to normal human skin, no local skin reaction or adverse effect could be detected.

Topical MMA ointment was applied to dermal wounds in a rat model. Adult Sprague-Dawley rats were used as the animal model. 10 mm skin punch biopsies were removed from the skin. Control and experimental wounds were created in each animal. 0.1 cc (150 mcg MMA) ointment was applied to all but control wounds and incisions were closed over the ointment with absorbable suture. Animals were euthanized and skin tissue was harvested at 2 weeks for gross and histologic analyses.

Figure 21:
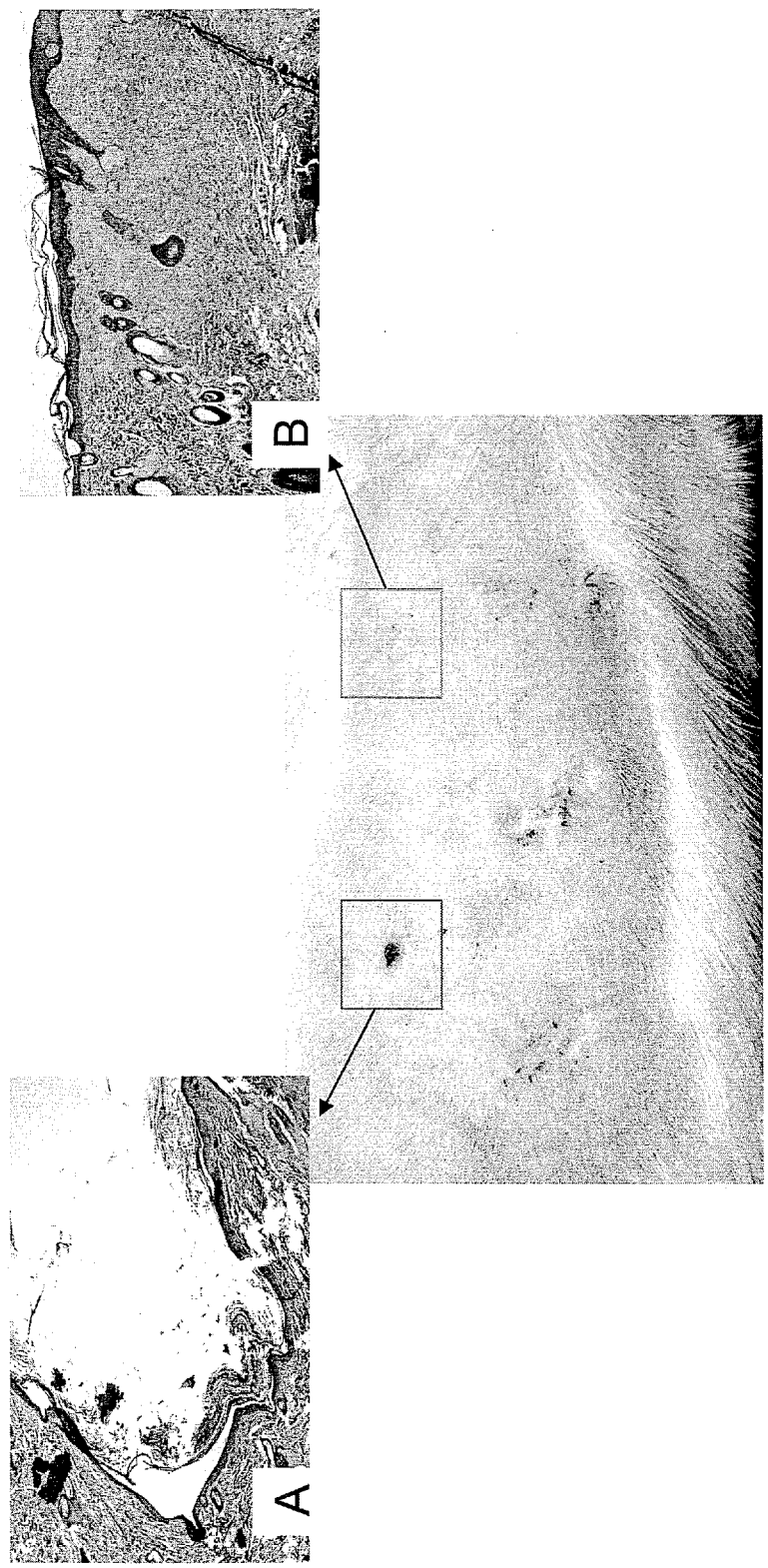
FIG. 21. Day 14, control no MMA ointment (A), MMA ointment (B). Note ulceration and depressed scar of control (A, red box) when compared to MMA-ointment wound (B, green box). No adverse gross or histologic tissue effects could be detected in MMA ointment animals (Masson's Trichrome, 4×).

All animals survived surgery. There were no wound infections. No local adverse wound effects could be detected grossly or histologically in MMA treated wounds. Control wounds showed a central depressed scar grossly and histologically; epithelium was poorly developed in control wounds when compared to MMA treated specimens. Collagen was reduced in MMA treated wounds when compared to controls (FIG. 21)

Topical MMA ointment was also applied to a human skin laceration. A single human volunteer sustained a deep laceration to the thumb while performing yardwork. The wound was cleaned in the usual sterile manner and 0.05-0.1 cc of 0.1% MMA ointment was applied twice daily for 5 days.

Figure 22:
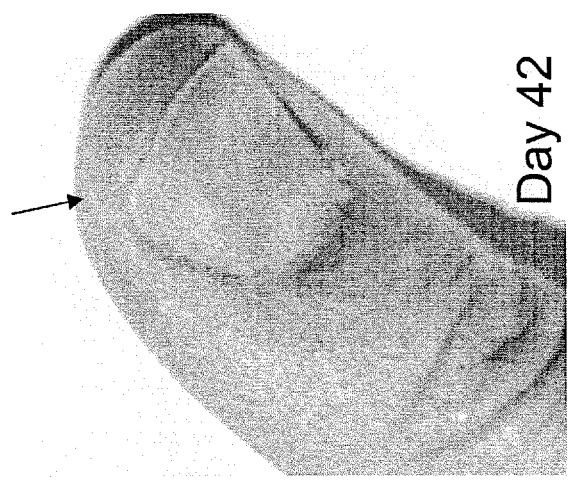
FIG. 22. Five day application of 0.1% MMA ointment to human thumb laceration (arrow). Note no adverse skin reaction was seen during early wound healing (Day 3). No visible scar could be detected at 42 days.
Figure 22:
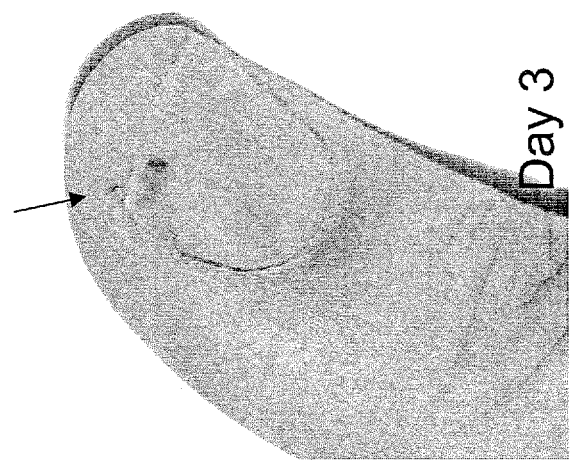
Figure 22:
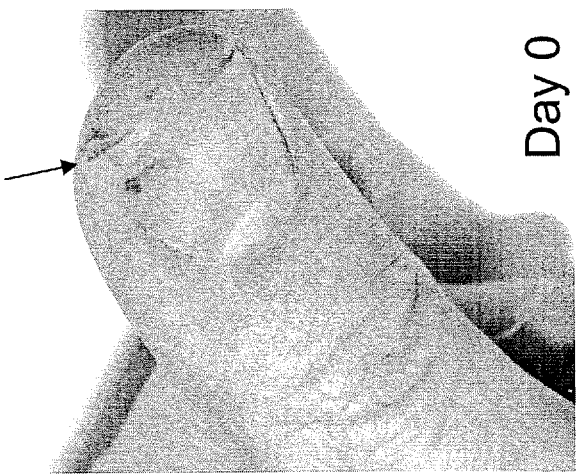

After twice daily application of MMA-ointment to a human skin laceration over a 5 day period, excellent wound healing was observed. No adverse reaction to the ointment could be detected and no scar could be visualized at 6 week timepoint (FIG. 22)

In conclusion, topical MMA-application in a water soluble base is feasible in animal and human models without local adverse effect on skin and with reduced scar tissue formation. A novel transdermal patch drag delivery system is demonstrated.

Example 11

Development of Mithramycin a Coated Surgical Sutures for the Prevention of Scar Tissue Formation Monocryl (M), polyglycolic acid (PGA) and silk (S) suture materials were selected for coating. Two coating methods were used for all three materials:

Method 1: Suture materials were cut into uniform 2 cm pieces heated for 15 seconds in a standard microwave oven in order to allow the surface of the suture to become more adherent. Suture materials were then placed in water based solution of MMA (500 mcg/ml), flash frozen in liquid nitrogen and stored at −80 F. Subsequently samples were vacuum dried, sterilized using ethylene oxide or gamma irradiation and set aside for in-vivo implantation.

Figure 23:
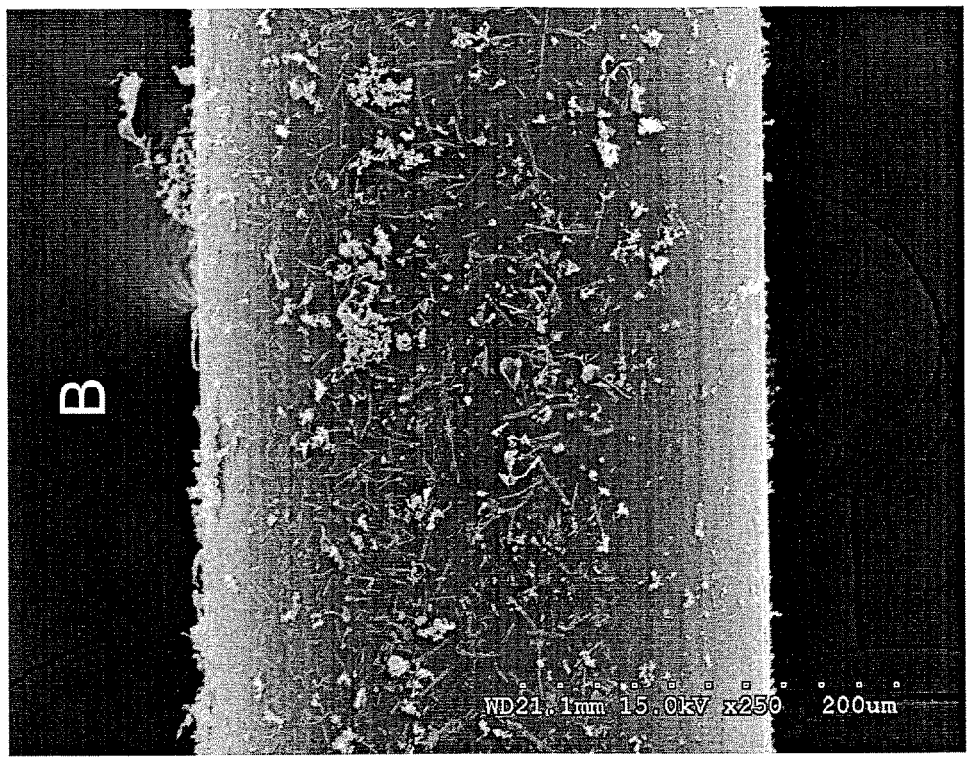
FIG. 23. Representative SEM photograph of uncoated 3.0 monocryl (A) and MMA-coated 3.0 monocryl suture (B) (15 kV).
Figure 23:
Figure 24:
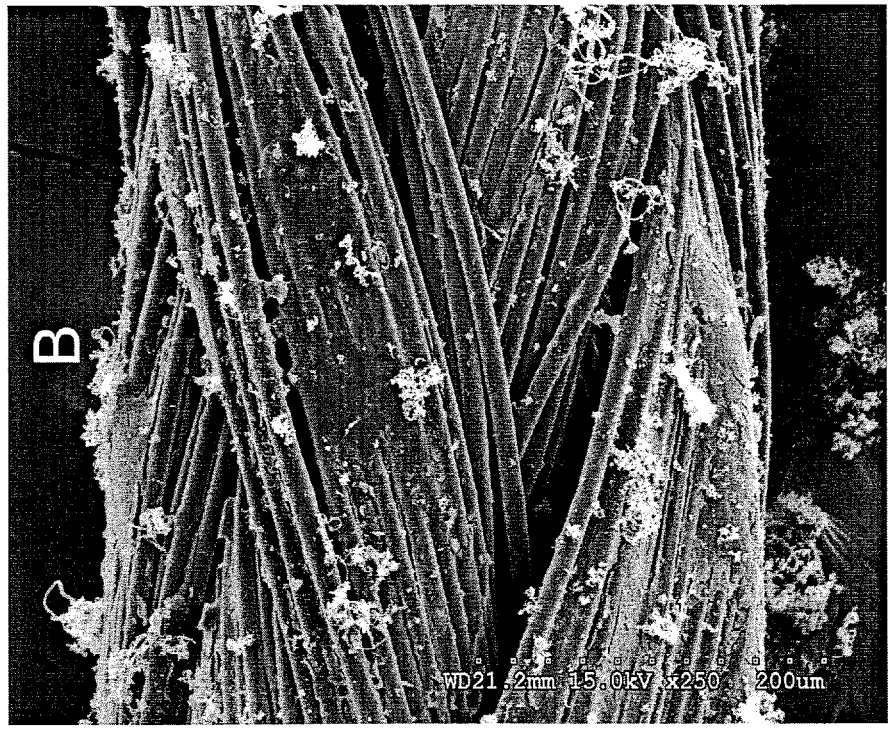
FIG. 24. Representative SEM photograph of uncoated (A) and MMA coated (B) braided polyglycolic acid (PGA) suture (15 kV).
Figure 24:
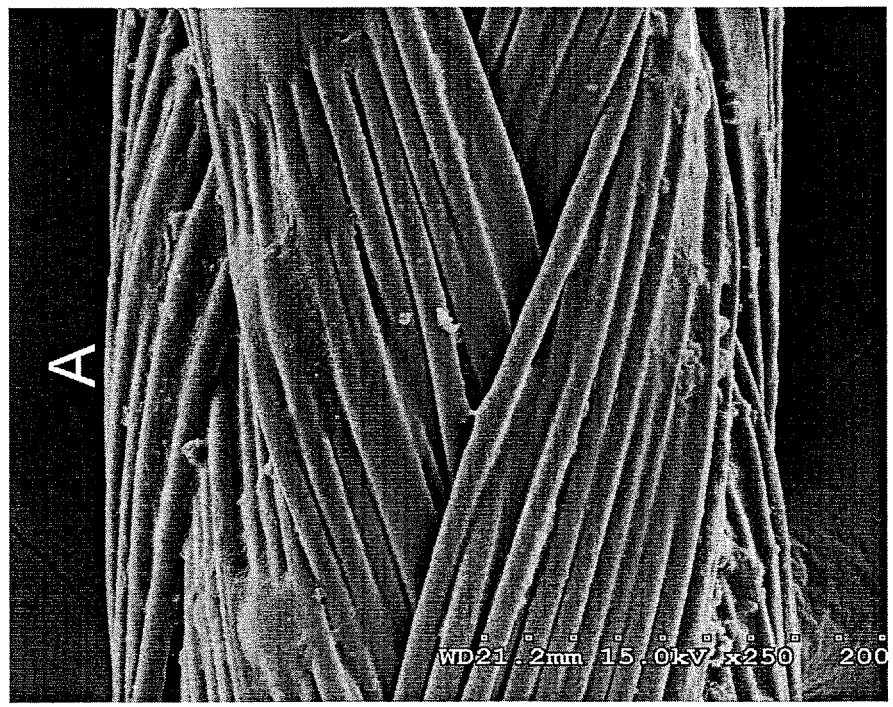

Method 2: Suture materials were cut into uniform 2 cm pieces flash frozen in liquid nitrogen for 5 minutes and then placed in a water based solution of MMA (500 mcg/ml) and flash frozen in liquid nitrogen and stored at −80 F. Subsequently samples were vacuum dried, sterilized using ethylene oxide or gamma irradiation and set aside for in-vivo implantation. Gross inspection and scanning electron microscopy were used to confirm the presence and distribution of drug particulate on suture materials. Gross inspection of coated suture showed a readily visible yellowish, crystalline material applied to silk, monocryl and polyglycolic acid suture material when compared to controls. Scanning electron microscopy (SEM) was carried out on randomly selected samples. Even distribution of drug particulate matter was visualized on all samples (FIGS. 23 and 24).

An in vitro MMA elution study was performed. The release of MMA from coated monocryl sutures into phosphate buffered saline (PBS) was used to estimate drug release in vivo. A 2.5 cm segment of 3.0 Monocryl suture was placed in 1.5 mL of PBS and incubated at 37° C. At 5, 15, 30, and 45 minutes and 1, 2, 4, 8, 24, 48, 72, and 96 hours the segment was transferred into a new 1.5 mL aliquot of PBS, and the amount of MMA from the previous aliquot was measured with UV spectrophotometry at 275 nm. Data from UV spectrophotometry indicated a rapid release of MMA into PBS in-vitro It was approximated that 90% of the total drug mass was released in 30 minutes and that the drug was nearly eliminated in 2 hours. An average in vitro drug concentration of $1.1 \times 10^{-5}$ M was achieved. A coating of approximately 50-100 mcg of drug/cm of suture was estimated.

In vivo implantation was also performed. MMA-coated and uncoated 3.0 monocryl sutures were cut into 2 cm pieces and implanted subcutaneously in the dorsum of adult Sprague-Dawley rats. 6 control and 12 experimental implantations were performed. Animals were euthanized and specimens harvested at 2 and 4 weeks for gross and histologic analyses. A total dose range of 100-200 mcg of drug was applied in each animal.

Figure 25:
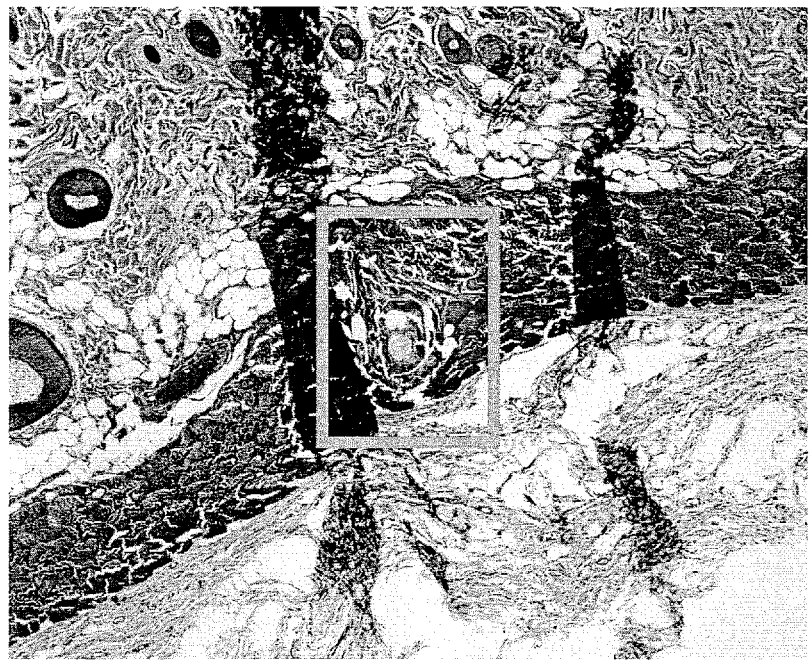
FIG. 25. Subcutaneous implant site at 14 days, 3.0 monocryl control (A) vs. MMA-coated 3.0 monocryl (B). Note intense inflammatory infiltrate and replacement of muscle by collagen in control specimen (A, yellow oval)) and relatively discreet deposition of collagen within muscle in MMA-coated implant (B, green rectangle). Masson's trichrome, 4×.
Figure 25:
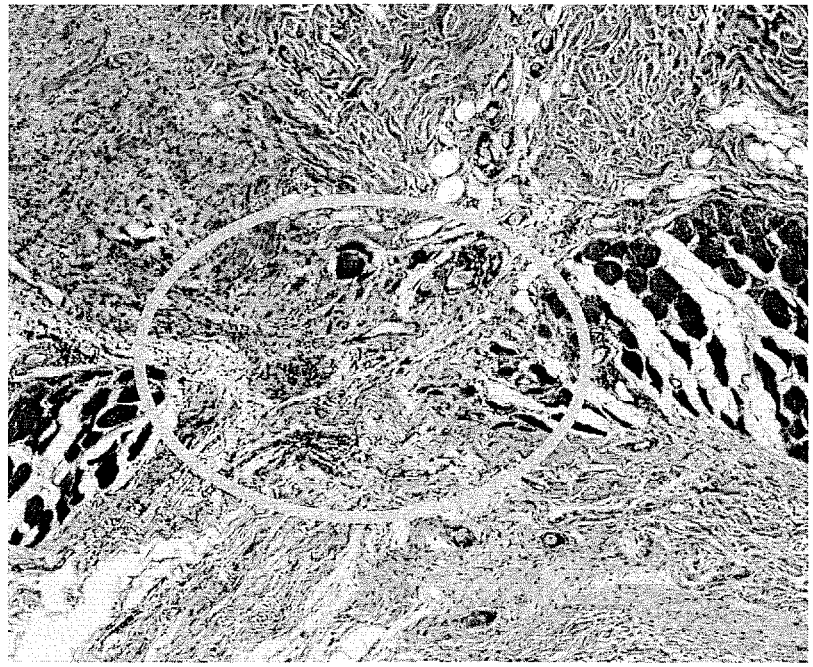
Figure 26:
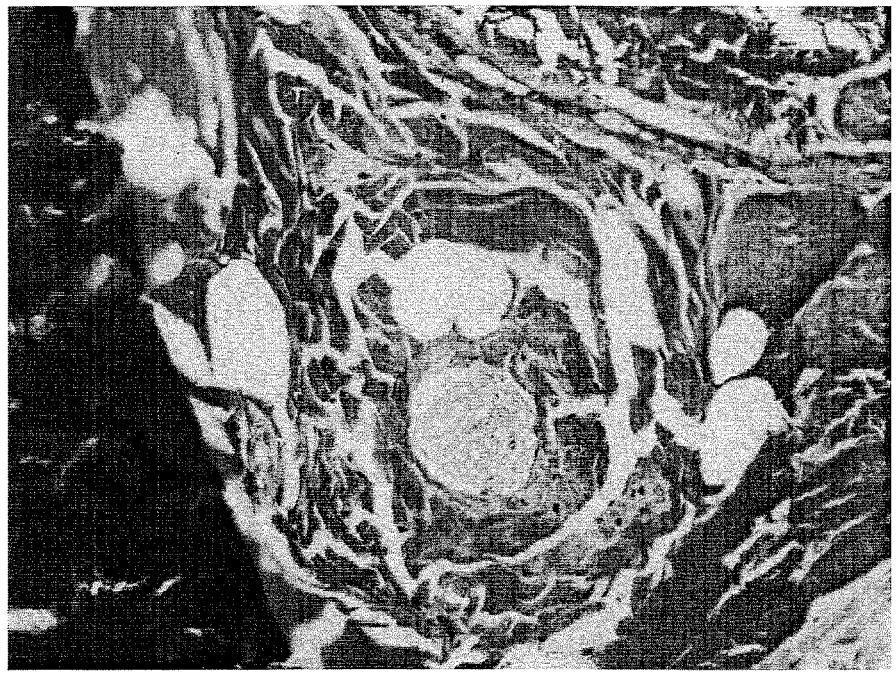
FIG. 26. Subcutaneous implant site at 14 days, 3.0 monocryl control (A) vs MMA-coated 3.0 monocryl (B). Note intense inflammatory infiltrate in control specimen (A) and relatively discreet deposition of collagen within muscle and lack of inflammatory cells in MMA-coated implant site (B) Masson's trichrome, 20×.
Figure 26:
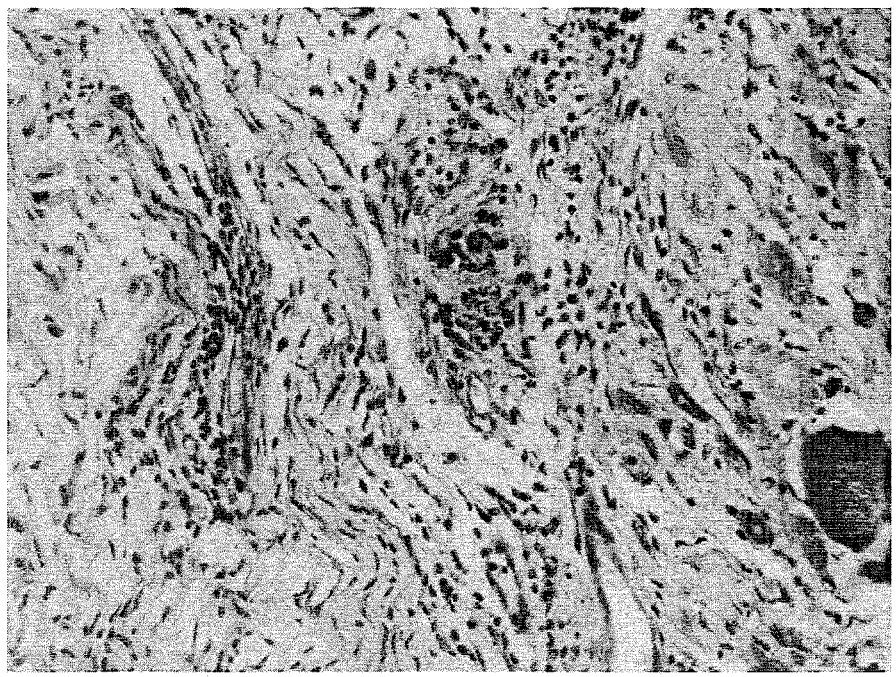
Figure 27:
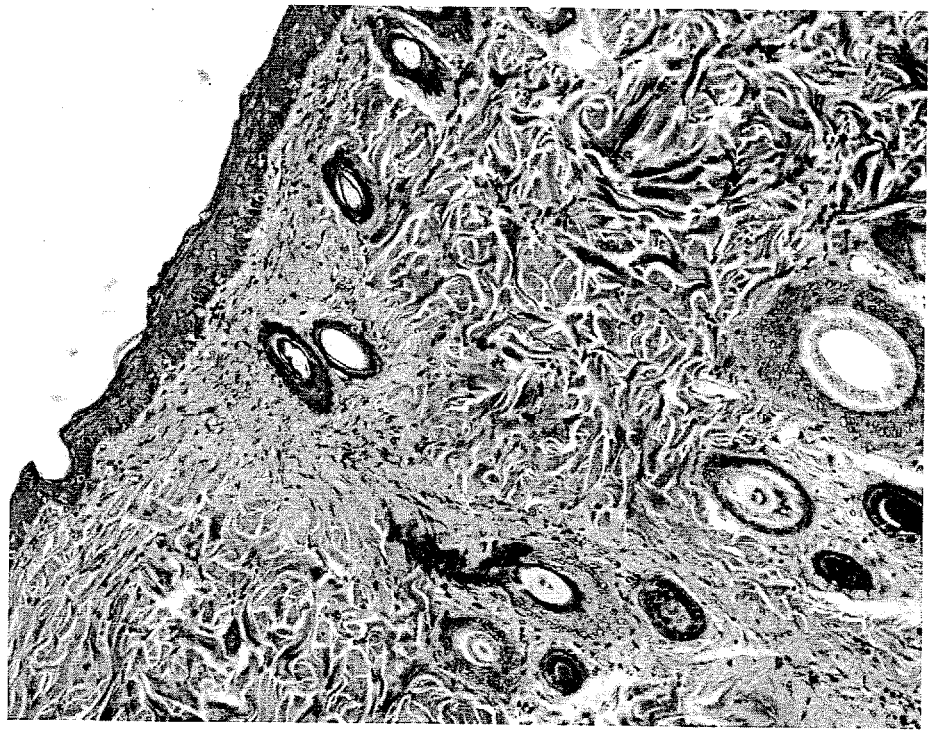
FIG. 27. Day 14 skin, control 3.0 monocryl suture implant (A) vs. MMA coated 3.0 monocryl implant. Note intense fibroblast response, wide deposition of collagen and poor epithithelialization of control compared to MMA-treated animal. Masson's trichrome, 10×.
Figure 27:

Control and MMA coated 3.0 monocryl suture implants were harvested at 2 and 4 weeks. All animals survived implantation of MMA-coated suture material. No gross or histologic adverse tissue reactions were noted during the study period. Less visible scar and inflammation was noted on skin of wounds implanted with MMA-coated 3.0 mococryl when compared to controls. Two and four week histologic data revealed decreased fibroblastic infiltrate and decreased collagen deposition at the subcutaneous implant site (muscle) (FIGS. 25 and 26) and at the skin site (FIG. 27) in MMA-coated animals when compared to controls.

In conclusion, this study demonstrates that mithramycin-A can be applied as a coating to various suture materials including silk, monocryl and polyglycolic acid. Microgram doses of MMA (100-200 mcg) resulted in decreased scarring in muscle and skin when compared to controls. Finally, no adverse systemic or local tissue effects were seen with microgram doses of MMA in rats.

Example 12

Absorbable Mithramycin-PLGA Stents

The following study provides PLGA stents containing mithramycin, which are useful for the treatment of coronary artery stenosis or vascular stenosis of the cerebrovascular and peripheral vasculature, esophageal stenosis, etc.

Biodegradable stents were fabricated by electrospinning using 15 w/v % poly(lactide-co-glycolide) (PLGA, molecular weight: 71 kDa, Lakeshore Biomaterials, Birmingham, Ala.) in 1,1,1,3,3,3-hexafluoro-2-propanol (99+%) (HFP, Sigma Chemical Co., St. Louis Mo.). 0.5 w/v % mithramycin was added to PLGA solution prior to electrospinning. The electrospinning set-up included a syringe pump, a high voltage supply, and a rotating mandrel (Custom Design & Fabrication, Richmond, Va.) to collect the fibers. A positive voltage (25 kV) was applied to the PLGA solution by the power supply (Spellman High Voltage, Hauppauge, N.Y.). The PLGA solution was delivered through an 18 gauge blunt tip syringe needle at a constant flow rate of 3 mL/hr using a syringe pump (Medfusion 2001, Medex, Inc., Carlsbad, Calif.). The collecting mandrel was a stainless steel rod (1.8 mm diameter). The distance between the syringe tip and the mandrel was 10 cm and the rotation rate was 1000 rpm. Stents made from PLGA without drug were used as a control, and these were fabricated using the same procedure.

A single long tubular stent with an internal diameter (ID) of 1.25 mm and an outer diameter(OD) of 2.25 mm was made from PLGA-only or MMA-PLGA The resulting single, long stents were then cut into 5 mm long segments for in-vivo implantation.

Gross inspection, scanning electron microscopy (SEM) and drug elution analyses were performed in-vitro on all stent materials. Gross inspection revealed that fabricated PLGA and MMA-PLGA stents showed a uniformly round, smooth hollow tube of specified dimensions with no significant surface irregularities. To confirm even incorporation of drug into the stent SEM was carried out of the surface and cross-sectional aspects of PLGA and MMA-PLGA stents. No significant difference could be seen between the surface or cross-sectional appearances of the PLGA and MMA-PLGA stents.

Fabricated MMA-PLGA stents were tested in-vitro to determine if drug would elute from the stent. Drug elution was performed by placing specimens in PBS on a shaker at 37° C. 500 mcl specimens of solution were drawn off systematically from 30 minutes to 120 h. Specimens were transferred into fresh PBS solution at each time interval. Stent degradation was observed grossly. When stents were placed in PBS solution MMA-PLGA stents fell to the bottom of the solution by 30 minutes suggesting ready water absorption due to presence of hydrophilic drug. UV spectrophotometry identified steady release of microgram quantities of drug into solution over a 152 hour time period. The concentration of drug in solution ranged from $1.48 \times 10^{-6}$ M to $2.9 \times 10^{-5}$ M.

In vivo tissue response and stent degradation were also tested. MMA-PLGA and PLGA-only stents were implanted subcutaneously on the dorsum of adult Sprague Dawley rats. Stents were harvested at 14 days, sectioned and stained with hematoxylin and eosin and Masson's Trichrome.

MMA-PLGA and PLGA stents were still present, but partially degraded in subcutaneous tissue at 14 days. MMA-PLGA stents appeared to show greater degradation than PLGA-only stents. Gross inspection of tissue showed no adverse tissue reaction. Tissue response was characterized by reduced chronic inflammatory infiltrate, reduced fibroblast counts and reduced collagen staining in MMA-PLGA stents when compared to PLGA-stents.

The foregoing is illustrative of the present invention, and is not to be construed as limiting thereof. The invention is defined by the following claims, with equivalents of the claims to be included therein.

That which is claimed is:

1. A biodegradable or non-biodegradable medical device comprising a substrate and a collagen inhibitor on or in said substrate,
   wherein said collagen inhibitor is selected from the group consisting of: mithramycin, mitomycin-c, tranilast, halofuginone and analogs thereof,
   wherein said device is a urethral catheter, ureteral stent, nephroureteral catheter, esophageal stent, tracheal stent, laryngeal/tracheal/pulmonary stent, nasal stent, salivary duct stent, biliary stent, enteric stent or nasolacrimal stent, and
   wherein said substrate is coated with said collagen inhibitor such that said collagen inhibitor is eluted from said medical device for a period of up to 8 days.

2. The medical device of claim 1, wherein said medical device is a stent.

3. The medical device of claim 1, wherein said substrate is comprised of a material selected from the group consisting of vinyl, polyethylene, poly(vinyl chloride) (PVC), ethylene vinyl acetate (EVA), silicone, latex, and polypropylene.

4. The medical device of claim 1, wherein said substrate comprises a biodegradable polymer selected from the group consisting of poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, and blends and copolymers thereof.

5. A method of treating an esophageal or tracheal stricture in a subject in need thereof comprising topically administering a collagen inhibitor in an amount effective to treat said stricture in said subject,
   said collagen inhibitor selected from the group consisting of: mithramycin, mitomycin-c, tranilast, halofuginone and analogs thereof,
   wherein said administering step is carried out by stenting said stricture with a biodegradable esophageal stent or tracheal stent according to claim 1 comprising said collagen inhibitor.

6. A kit comprising:
   (a) a medical device comprising a substrate coated with a collagen inhibitor,
   wherein said collagen inhibitor is selected from the group consisting of: mithramycin, mitomycin-c, tranilast, halofuginone and analogs thereof,
   wherein said medical device is a urethral catheter, ureteral stent, nephroureteral catheter, esophageal stent, tracheal stent, laryngeal/tracheal/pulmonary stent, nasal stent, salivary duct stent, biliary stent, enteric stent or nasolacrimal stent, and
   wherein said substrate is coated with said collagen inhibitor such that said collagen inhibitor is eluted from said medical device for a period of up to 8 days; and
   (b) a container in which said medical device is packaged in sterile form.

7. The kit of claim 6, wherein said container comprises a plastic or foil container.

8. The kit of claim 6, wherein said container is vacuum-packed.

9. The kit of claim 6, wherein said substrate is coated with a single unit dose of said collagen inhibitor.

10. The kit of claim 6, wherein said substrate is biodegradable or bioabsorbable.

11. The medical device of claim 1, wherein said device is a biliary stent.

12. The medical device of claim 1, wherein said device is an enteric stent.

13. The medical device of claim 1, wherein said device is an esophageal stent.

14. The medical device of claim 1, wherein said device is a tracheal stent.

15. The medical device of claim 1, wherein said device is a urethral catheter, ureteral stent or nephroureteral catheter.

16. The medical device of claim 1, wherein said collagen inhibitor is halofuginone.

17. The medical device of claim 1, wherein said substrate is coated with the collagen inhibitor such that said collagen inhibitor is eluted from the medical device in an amount effective to inhibit collagen production with substantially no cell toxicity.

18. The kit of claim 6, wherein said collagen inhibitor is halofuginone.

19. A biodegradable or bioabsorbable medical device comprising a substrate and a collagen inhibitor,
   wherein said device is a urethral catheter, ureteral stent, nephrourteral catheter, esophageal stent, laryngeal/tracheal/pulmonary stent, nasal stent, salivary duct stent, biliary stent, enteric stent or nasolacrimal stent,
   wherein said substrate is coated with said collagen inhibitor such that said collagen inhibitor is eluted from said medical device for a period of up to 8 days.

20. The biodegradable or bioabsorbable medical device of claim 19, wherein said collagen inhibitor is selected from the group consisting of mithramycin, mitomycin-c, tranilast, halofuginone and analogs thereof.

21. The biodegradable or bioabsorbable medical device of claim 19, wherein said substrate is coated with a collagen inhibitor selected from the group consisting is halofuginone or mithramycin.

22. The biodegradable or bioabsorbable medical device of claim 19, wherein said substrate is impregnated with a collagen inhibitor selected from the group consisting is halofuginone or mithramycin.

23. The biodegradable or bioabsorbable medical device of claim 19, wherein said substrate comprises one or more biodegradable polymers selected from the group consisting of poly(lactide)s, poly(glycolide)s, poly(lactide-coglycolide)s, poly(lactic acid)s, poly(glycolic acid)s, poly(lactic acid-coglycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, and blends and copolymers thereof.

24. The biodegradable or bioabsorbable medical device of claim 19, wherein said substrate is coated with the collagen inhibitor such that said collagen inhibitor is eluted from the medical device in an amount effective to inhibit collagen with substantially no cell toxicity.

25. The biodegradable or bioabsorbable medical device of claim 19, wherein said device is a biliary stent.

26. The biodegradable or bioabsorbable medical device of claim 19, wherein said device is an enteric stent.

27. The biodegradable or bioabsorbable medical device of claim 19, wherein said device is an esophageal stent.

28. The biodegradable or bioabsorbable medical device of claim 19, wherein said device is a urethral catheter, ureteral stent or nephroureteral catheter.

29. A medical device comprising a substrate coated or impregnated with halofuginone or mithramycin,
wherein said device is a urethral catheter, ureteral stent, nephrourteral catheter, esophageal stent, laryngeal/tracheal/pulmonary stent, nasal stent, salivary duct stent, biliary stent, enteric stent or nasolacrimal stent, and
wherein said substrate is coated with said collagen inhibitor such that said collagen inhibitor is eluted from said medical device for a period of up to 8 days.

30. The medical device of claim 29, wherein said substrate comprises a material selected from the group consisting of silicone, silastic, latex, polyurethane and poly(lactide-coglycolide).

31. The medical device of claim 29, wherein said substrate is coated or impregnated with halofuginone.

32. The medical device of claim 29, wherein said substrate is coated with the collagen inhibitor such that said collagen inhibitor is eluted from the medical device in an amount effective to inhibit collagen with substantially no cell toxicity.

33. The medical device of claim 29, wherein said device is a biliary stent.

34. The medical device of claim 29, wherein said device is an enteric stent.

35. The medical device of claim 29, wherein said device is an esophageal stent.

36. The medical device of claim 29, wherein said device is a urethral catheter, ureteral stent or nephroureteral catheter.

37. The medical device of claim 29, wherein said device is a ureteral stent or nephroureteral catheter.

* * * * *

UNITED STATES PATENT AND TRADEMARK OFFICE
CERTIFICATE OF CORRECTION

| | | |
|---|---|---|
| PATENT NO. | : 8,883,183 B2 | Page 1 of 1 |
| APPLICATION NO. | : 12/130614 | |
| DATED | : November 11, 2014 | |
| INVENTOR(S) | : Sullivan et al. | |

It is certified that error appears in the above-identified patent and that said Letters Patent is hereby corrected as shown below:

On Title Page:
Please add the following items to the Title page after item (22):

Related U.S. Application Data

(63) Continuation-in-part of application No. 11/948,294, filed on Nov. 30, 2007.

(60) Provisional application No. 60/868,217, filed on Dec. 1, 2006.

In the Specification:
Column 12, Line 7: Please correct "$10^{11}$ or" to read -- $10^{-11}$ or --

Signed and Sealed this
Thirty-first Day of March, 2015

Michelle K. Lee
*Director of the United States Patent and Trademark Office*